United States Patent
Bai et al.

(10) Patent No.: US 9,346,818 B2
(45) Date of Patent: May 24, 2016

(54) BENZODIOXOLE DERIVATIVE AND PREPARATION METHOD AND USE THEREOF

(71) Applicant: Zhejiang Hisun Pharmaceutical Co., Ltd., Taizhou (CN)

(72) Inventors: Hua Bai, Taizhou (CN); Xuyang Zhao, Chengdu (CN); Jinqing Zhong, Taizhou (CN); Yongxiang Gong, Taizhou (CN); Qifeng Zhu, Taizhou (CN); Xiaoyu Liu, Taizhou (CN); Xiaohe Zheng, Taizhou (CN); Lifei Liu, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 14/411,783

(22) PCT Filed: Jul. 3, 2013

(86) PCT No.: PCT/CN2013/000813
§ 371 (c)(1),
(2) Date: Dec. 29, 2014

(87) PCT Pub. No.: WO2014/005421
PCT Pub. Date: Jan. 9, 2014

(65) Prior Publication Data
US 2015/0191480 A1    Jul. 9, 2015

(30) Foreign Application Priority Data
Jul. 3, 2012   (CN) .......................... 2012 1 0226125

(51) Int. Cl.
| C07D 401/06 | (2006.01) |
| C07D 491/056 | (2006.01) |
| A61K 31/435 | (2006.01) |
| A61K 31/4523 | (2006.01) |
| C07D 491/04 | (2006.01) |
| C07D 491/113 | (2006.01) |

(52) U.S. Cl.
CPC .......... *C07D 491/056* (2013.01); *A61K 31/435* (2013.01); *A61K 31/4523* (2013.01); *C07D 401/06* (2013.01); *C07D 491/04* (2013.01); *C07D 491/113* (2013.01)

(58) Field of Classification Search
CPC ............. A61K 31/435; A61K 31/4523; C07D 401/06; C07D 491/04; C07D 491/56; C07D 491/113
USPC .................... 514/252.03, 256, 278, 318, 321; 544/230, 238; 546/15, 193, 198
See application file for complete search history.

(56) References Cited

U.S. PATENT DOCUMENTS 4,087,541 A * 5/1978 Eberlein ............... C07C 309/00 514/411
4,895,841 A    1/1990 Sugimoto et al.
5,100,901 A    3/1992 Sugimoto et al.
5,175,157 A * 12/1992 Psiorz .................. C07D 223/16 514/212.06
2009/0137629 A1    5/2009 Iimura et al.

FOREIGN PATENT DOCUMENTS

| CN | 1426405 A | 6/2003 |
| CN | 101626688 A | 1/2010 |
| EP | 0296560 | * 12/1988 |
| EP | 1260512 A1 | 11/2002 |
| WO | 0009483 A2 | 2/2000 |
| WO | 2005003092 A1 | 1/2005 |
| WO | 2005076749 A2 | 8/2005 |
| WO | 2007077443 A1 | 7/2007 |
| WO | 2007082731 A1 | 7/2007 |

OTHER PUBLICATIONS

Eberlein et al. "2-arylalkylaminoalkyl-phenalimidines" CA89:109088 (1978).*
Psiora et al. "Preparation and . . . " CA119:8698 (1993).*
Sugimoto, et al., Synthesis and Structure—Activity Relationships of Acetylcholinesterase Inhibitors: 1-Benzyl-4-[(5,6-dimethoxy-1-oxoindan-2-yl)methyl] piperidineHydrochloride and Related Compounds, J. Med. Chem. 1995, 38, 4821-4829; 1995 American Chemical Society.
William Thies, Ph.D, and Laura Bleiler, Alzheimer's Association Report 2011 Alzheimer's disease facts and figures, Alzheimer's & Dementia 7 (2011) 208-244.
Terry, Buccafusco, et al., The Prototypical Ranitidine Analog JWS-USC-75-IX Improves Information Processing and Cognitive Function in Animal Models. The Journal of Pharmacology and Experimental Therapeutics, vol. 336, No. 3, 2011.
Wilkins Reeve and Herbert Myers, The Systheses of Hydrastic Acid, Department of Chemistry, University of Buffalo, 1951.
Edward Leete. Biosynthesis of the Alkaloids of Chelidonium majus. I. The incorporation of Tyrosine into Chelidonine, p. 473, 1963.
International Search Report for Application No. PCT/CN2013/000813 dated Oct. 17, 2013.

* cited by examiner

Primary Examiner — Celia Chang
(74) Attorney, Agent, or Firm — Lerner, David, Littenberg, Krumholz & Mentlik, LLP

(57) ABSTRACT

Provided in the present invention are novel benzodioxole derivatives and preparation methods thereof. These compounds represented by formula (I) or pharmaceutically acceptable salts thereof have acetylcholinesterase inhibitory activity, so can be used in the treatment or prevention of Alzheimer's disease. The definitions of $R^1$, $R^2$ and A of formula (I) can be seen in the description.

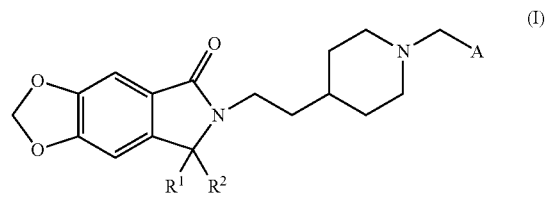

25 Claims, 1 Drawing Sheet

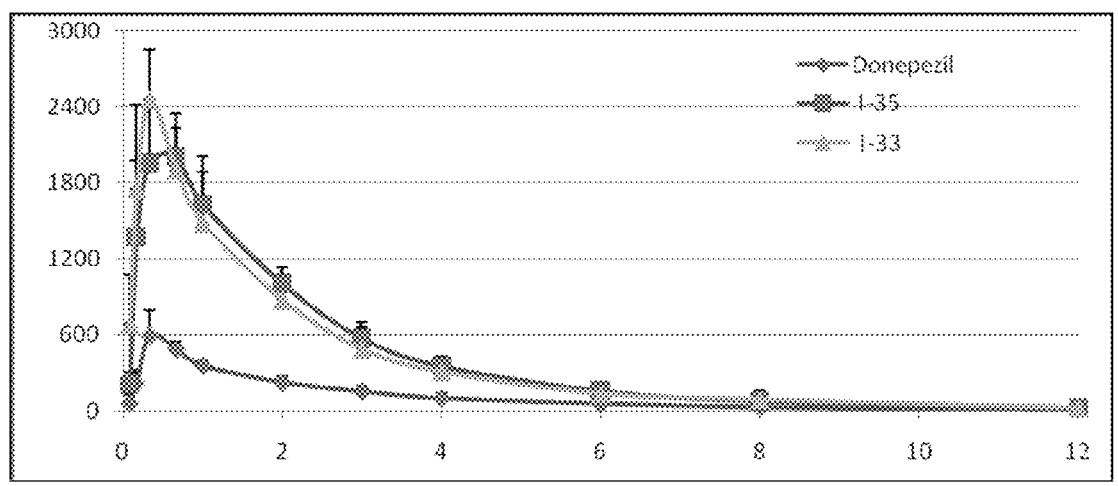

BENZODIOXOLE DERIVATIVE AND PREPARATION METHOD AND USE THEREOF

CROSS-REFERENCE TO RELATED APPLICATIONS

The present application is a national phase entry under 35 U.S.C. §371 of International Application No. PCT/CN2013/000813 filed Jul. 3, 2013, published in Chinese, which claims priority from Chinese Patent Application No. 201210226125.7, filed Jul. 3, 2012, all of which are incorporated herein by reference.

FIELD OF THE INVENTION

The present invention relates to a class of novel benzodioxole derivatives. These compounds have inhibitory activity on acetylcholinesterase, thus can be used in the treatment or prevention of Alzheimer's disease. The present invention also relates to the preparation method of these compounds.

BACKGROUND OF THE INVENTION

With the increasement of the population of elder peoples, the population suffering Alzheimer's disease increases rapidly. Alzheimer's disease is also referred to as Alzheimer type dementia or senile dementia of the Alzheimer type. Currently, although the incidence of this disease worldwide is unknown, according to the latest report from Alzheimer's Association of the United States, about 5.4 million of people suffering Alzheimer's disease until 2011 in the United States, and the population suffering this disease in the United States will increase to about 13.5 million until 2050 in the United States. Therefore, there is an urgent need for developing novel drugs for the treatment of this disease with higher efficiency and lower adverse effects.

Alzheimer's disease is the most common senile dementia, and has become the 6th cause of death of American, and the 5 th cause of death of American aged 65 or older. Although this disease has been researched widely and deeply by scientists, the exact reason causing this disease is still unknown. Alzheimer's disease is a progressive disease, and it kills nerve cells continuously and breaks the neural connections in brain, resulting in the break of the tissues in brain, and in turn resulting in the loss of memory, consciousness, and judgment of patients, as well as emotional disorder and behavior disorder in the patients.

Alzheimer's disease is a kind of irreversible disease, and there is no drug can prevent this disease and there is also no drug can cure this disease or prolong the progress of this disease. Nowadays, the drugs for treating this disease can only relieve or improve the symptom of this disease. There are 5 drugs that have been approved by FDA of United States, wherein 4 of them are inhibitors of acetylcholinesterase. Acetylcholine is a kind of neurotransmitter, and is a chemical substance released by nerves. If the system generating acetylcholine, i.e. the cholinergic system, in the brain is broken, memory disorder associated with Alzheimer's disease will be caused. Whereas, the function of acetylcholinesterase is to catalyze the hydrolysis of acetylcholine, i.e., to degrade acetylcholine. Since Alzheimer's disease is accompanied with the decay of acetylcholine activity, the inhibition of acetylcholinesterase is thus one of the approaches for treating this disease. As mentioned above, 4 of the 5 drugs that have been used for the treatment of Alzheimer's disease in clinical are inhibitors of acetylcholinesterase. There inhibitors of acetylcholinesterase include donepezil, tacrine, rivastigmine and galantamine, wherein donepezil is the first-line drug for the treatment of Alzheimer's disease (Sugimoto et al. U.S. Pat. Nos. 4,895,841 and 5,100,901; Pathi et al. WO 2007077443; Parthasaradhi et al. WO 2005003092; Dubey et al. WO 2005076749; Gutman et al. WO 200009483; Sugimoto et al. J. Med. Chem. 1995, 38, 4821). However, donepezil and the other 4 drugs can only improve the condition of patients, and such improvement is only transient, i.e. can only last 6-12 months, and also, the response rates of the patients to these drugs are only about 50% (Alzheimer's Association, 2011 Alzheimer' Disease Facts and Figures, Alzheimer's & Dementia, 2011, 7(2), 208). The present invention provides novel acetylcholinesterase inhibitors, which are novel benzodioxole derivatives and are drugs for the treatment of Alzheimer' disease, having higher efficiency and lower adverse effects in comparison to donepezil.

DETAILED DESCRIPTION

One of the objects of the present invention is to provide novel inhibitors of acetylcholinesterase, benzodioxole derivatives or pharmaceutically acceptable salts thereof.

The compounds of the present invention can be represented by formula (I):

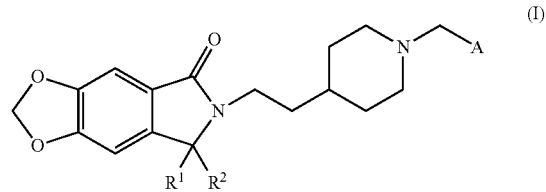

wherein, $R^1$ and $R^2$ are independently selected from the group consisting of hydrogen, methyl and ethyl; $R^1$ and $R^2$ together can be =O; also, $R^1$ and $R^2$ together with the carbon atom connecting them can form a 3-membered carbon ring;

A is selected from the group consisting of phenyl, $R^3$-substituted phenyl, pyridinyl, $R^4$-substituted pyridinyl, pyrimidinyl, $R^5$-substituted pyrimidinyl, pyrrolyl, $R^6$-substituted pyrrolyl, pyridazinyl, $R^7$-substituted pyridazinyl, pyrazolyl, and $R^8$-substituted pyrazolyl;

$R^3$ is 1 to 5 substituents independently selected from the group consisting of halogen, ($C_1$-$C_3$) alkyl, ($C_2$-$C_3$) alkenyl, ($C_3$-$C_4$) cycloalkyl, ($C_1$-$C_3$) alkoxy, trifluoromethyl and cyano;

$R^4$ is 1 to 4 substituents independently selected from the group consisting of halogen, ($C_1$-$C_3$) alkyl, ($C_2$-$C_3$) alkenyl, ($C_3$-$C_4$) cycloalkyl, ($C_1$-$C_3$) alkoxy, trifluoromethyl and cyano;

$R^5$ is 1 to 3 substituents independently selected from the group consisting of halogen, ($C_1$-$C_3$) alkyl, ($C_2$-$C_3$) alkenyl, ($C_3$-$C_4$) cycloalkyl, ($C_1$-$C_3$) alkoxy, trifluoromethyl and cyano;

$R^6$ is 1 to 4 substituents independently selected from the group consisting of ($C_1$-$C_3$) alkyl, ($C_2$-$C_3$) alkenyl, and ($C_3$-$C_4$) cycloalkyl;

$R^7$ is 1 to 3 substituents independently selected from the group consisting of halogen, ($C_1$-$C_3$) alkyl, ($C_2$-$C_3$) alkenyl, ($C_3$-$C_4$) cycloalkyl, ($C_1$-$C_3$) alkoxy, trifluoromethyl and cyano;

$R^8$ is 1 to 3 substituents independently selected from the group consisting of ($C_1$-$C_3$) alkyl, ($C_2$-$C_3$) alkenyl, and ($C_3$-$C_4$) cycloalkyl;

or a pharmaceutically acceptable salt thereof.

In another embodiment, A is preferably selected from phenyl, $R^3$-substituted phenyl, pyridinyl, $R^4$-substituted pyridinyl, pyrimidinyl, or $R^5$-substituted pyrimidinyl.

In another embodiment, wherein the above mentioned $R^1$ and $R^2$ are preferably hydrogen or methyl; $R^1$ and $R^2$ together are =O; or $R^1$ and $R^2$ together with the carbon atom connecting them form a 3-membered carbon ring; more preferably, $R^1$ and $R^2$, together with the carbon atom connecting them form a 3-membered carbon ring.

In another embodiment, wherein the above mentioned A is preferably phenyl, $R^3$-substituted phenyl, pyridinyl, $R^4$-substituted pyridinyl, pyrimidinyl, $R^5$-substituted pyrimidinyl, pyrrolyl, $R^6$-substituted pyrrolyl, pyridazinyl, $R^7$-substituted pyridazinyl, pyrazolyl, or $R^8$-substituted pyrazolyl; wherein $R^3$ is 1 to 5 substituents preferably selected from the group consisting of halogen, ($C_1$-$C_3$) alkyl, ($C_1$-$C_3$) alkoxy, trifluoromethyl and cyano; $R^4$ is 1 to 4 substituents preferably selected from the group consisting of halogen, ($C_1$-$C_3$) alkyl, ($C_1$-$C_3$) alkoxy, trifluoromethyl and cyano; $R^5$ is 1 to 3 substituents preferably selected from the group consisting of halogen, ($C_1$-$C_3$) alkyl, ($C_1$-$C_3$) alkoxy, trifluoromethyl and cyano; $R^6$ is 1 to 4 substituents preferably selected from ($C_1$-$C_3$) alkyl; $R^7$ is 1 to 3 substituents preferably selected from the group consisting of halogen, ($C_1$-$C_3$) alkyl, ($C_1$-$C_3$) alkoxy, trifluoromethyl and cyano; and $R^8$ is 1 to 3 substituents preferably selected from ($C_1$-$C_3$) alkyl.

In another embodiment, wherein the above mentioned A is more preferably phenyl, $R^3$-substituted phenyl, pyridinyl, pyrimidinyl, pyrrolyl, $R^6$-substituted pyrrolyl, pyridazinyl, or pyrazolyl; wherein $R^3$ is 1 to 5 substituents preferably selected from the group consisting of halogen, ($C_1$-$C_3$) alkyl, ($C_1$-$C_3$) alkoxy, trifluoromethyl and cyano; and $R^6$ is 1 to 4 substituents preferably selected from ($C_1$-$C_3$) alkyl.

Most preferably, A is phenyl, 2-fluorophenyl, 3-fluorophenyl, 4-fluorophenyl, 2,6-difluorophenyl, 2-pyridinyl, 3-pyridinyl, pyrimidin-2-yl, pyrrol-2-yl, 5-methyl pyrrol-2-yl, pyridazin-3-yl or 1H-pyrazol-5-yl.

More particularly, said compound of formula (I) is selected from:

6-[2-(1-benzyl-4-piperidyl)ethyl]-[1,3]dioxolo[4,5-f]isoindole-5,7-dione (I-1);

6-[2-[1-[(2-fluorophenyl)methyl]-4-piperidyl]ethyl]-[1,3]dioxolo[4,5-f]isoindole-5,7-dione (I-2);

6-[2-[1-[(3-fluorophenyl)methyl]-4-piperidyl]ethyl]-[1,3]dioxolo[4,5-f]isoindole-5,7-dione (I-3);

6-[2-[1-[(4-fluorophenyl)methyl]-4-piperidyl]ethyl]-[1,3]dioxolo[4,5-f]isoindole-5,7-dione (I-4);

6-[2-(1-benzyl-4-piperidyl)ethyl]-5H-[1,3]dioxolo[4,5-f]isoindol-7-one (I-5);

6-[2-[1-[(2-fluorophenyl)methyl]-4-piperidyl]ethyl]-5H-[1,3]dioxolo[4,5-f]isoindol-7-one (I-6);

6-[2-[1-[(3-fluorophenyl)methyl]-4-piperidyl]ethyl]-5H-[1,3]dioxolo[4,5-f]isoindol-7-one (I-7);

6-[2-[1-[(4-fluorophenyl)methyl]-4-piperidyl]ethyl]-5H-[1,3]dioxolo[4,5-f]isoindol-7-one (I-8);

6-[2-(1-benzyl-4-piperidyl)ethyl]-5-methyl-5H-[1,3]dioxolo[4, 5-f]isoindol-7-one (I-9);

6-[2-[1-[(2-fluorophenyl)methyl]-4-piperidyl]ethyl]-5-methyl-5H-[1,3]dioxolo[4,5-f]isoindol-7-one (I-10);

6-[2-[1-[(3-fluorophenyl)methyl]-4-piperidyl]ethyl]-5-methyl-5H-[1,3]dioxolo[4,5-f]isoindol-7-one (I-11);

6-[2-[1-[(4-fluorophenyl)methyl]-4-piperidyl]ethyl]-5-methyl-5H-[1,3]dioxolo[4,5-f]isoindol-7-one (I-12);

6-[2-(1-benzyl-4-piperidyl)ethyl]-7,7-dimethyl-[1,3]dioxolo[4,5-f]isoindol-5-one (I-13);

6-[2-[1-[(2-fluorophenyl)methyl]-4-piperidyl]ethyl]-7,7-dimethyl-[1,3]dioxolo[4,5-f]isoindol-5-one (I-14);

6-[2-[1-[(3-fluorophenyl)methyl]-4-piperidyl]ethyl]-7,7-dimethyl-[1,3]dioxolo[4,5-f]isoindol-5-one (I-15);

6-[2-[1-[(4-fluorophenyl)methyl]-4-piperidyl]ethyl]-7,7-dimethyl-[1,3]dioxolo[4,5-f]isoindol-5-one (I-16);

6-[2-(1-benzyl-4-piperidyl)ethyl]spiro[[1,3]dioxolo[4,5-f]isoindole-7,1'-cyclopropane]-5-one (I-17);

6-[2-[1-[(2-fluorophenyl)methyl]-4-piperidyl]ethyl]spiro[[1,3]dioxolo[4,5-f]isoindole-7,1'-cyclopropane]-5-one (I-18);

6-[2-[1-[(3-fluorophenyl)methyl]-4-piperidyl]ethyl]spiro[[1,3]dioxolo[4,5-f]isoindole-7,1'-cyclopropane]-5-one (I-19);

6-[2-[1-[(4-fluorophenyl)methyl]-4-piperidyl]ethyl]spiro[[1,3]dioxolo[4,5-f]isoindole-7,1'-cyclopropane]-5-one (I-20);

6-[2-[1-[(2-chlorophenyl)methyl]-4-piperidyl]ethyl]spiro[[1,3]dioxolo[4,5-f]isoindole-7,1'-cyclopropane]-5-one (I-21);

6-[2-[1-[[2-(trifluoromethyl)phenyl]methyl]-4-piperidyl]ethyl]spiro[[1,3]dioxolo[4,5-f]isoindole-7,1'-cyclopropane]-5-one (I-22);

6-[2-[1-(o-tolylmethyl)-4-piperidyl]ethyl]spiro[[1,3]dioxolo[4,5-f]isoindole-7,1'-cyclopropane]-5-one (I-23);

6-[2-[1-[(2-cyanophenyl)methyl]-4-piperidyl]ethyl]spiro[[1,3]dioxolo[4,5-f]isoindole-7,1'-cyclopropane]-5-one (I-24);

6-[2-[1-[(2,6-difluorophenyl)methyl]-4-piperidyl]ethyl]spiro[[1,3]dioxolo[4,5-f]isoindole-7,1'-cyclopropane]-5-one (I-25);

6-[2-[1-[(2-methoxyphenyl)methyl]-4-piperidyl]ethyl]spiro[[1, 3]dioxolo[4,5-f]isoindole-7,1'-cyclopropane]-5-one (I-26);

6-[2-[1-[(3-methoxyphenyl)methyl]-4-piperidyl]ethyl]spiro[[1, 3]dioxolo[4,5-f]isoindole-7,1'-cyclopropane]-5-one (I-27);

6-[2-[1-[(4-methoxyphenyl)methyl]-4-piperidyl]ethyl]spiro[[1, 3]dioxolo[4,5-f]isoindole-7,1'-cyclopropane]-5-one (I-28);

6-[2-[1-(2-pyridylmethyl)-4-piperidyl]ethyl]spiro[[1,3]dioxolo[4,5-f]isoindole-7,1'-cyclopropane]-5-one (I-29);

6-[2-[1-(3-pyridylmethyl)-4-piperidyl]ethyl]spiro[[1,3]dioxolo[4,5-f]isoindole-7,1'-cyclopropane]-5-one (I-30);

6-[2-[1-(4-pyridylmethyl)-4-piperidyl]ethyl]spiro[[1,3]dioxolo[4,5-f]isoindole-7,1'-cyclopropane]-5-one (I-31);

6-[2-[1-(pyrimidin-2-ylmethyl)-4-piperidyl]ethyl]spiro[[1, 3]dioxolo[4,5-f]isoindole-7,1'-cyclopropane]-5-one (I-32);

6-[2-[1-(2-pyridylmethyl)-4-piperidyl]ethyl]spiro[[1,3]dioxolo[4,5-f]isoindole-7,1'-cyclopropane]-5-one hydrochloride (I-33);

6-[2-(1-benzyl-4-piperidyl)ethyl]spiro[[1,3]dioxolo[4,5-f]isoindole-7,1'-cyclopropane]-5-one hydrochloride (I-34);

6-[2-[1-(2-pyridylmethyl)-4-piperidyl]ethyl]spiro[[1,3]dioxolo[4,5-f]isoindole-7,1'-cyclopropane]-5-one phosphate (I-35);

6-[2-[1-(2-pyridylmethyl)-4-piperidyl]ethyl]-[1,3]dioxolo[4,5-f]isoindole-5,7-dione (I-36);

6-[2-[1-(pyridazin-3-ylmethyl)-4-piperidyl]ethyl]-[1,3]dioxolo[4,5-f]isoindole-5,7-dione (I-37);

6-[2-[1-(pyridazin-3-ylmethyl)-4-piperidyl]ethyl]spiro[[1,3]dioxolo[4,5-f]isoindole-7,1'-cyclopropane]-5-one (I-38);

6-[2-[1-(1H-pyrrol-2-ylmethyl)-4-piperidyl]ethyl]spiro[[1,3]dioxolo[4,5-f]isoindole-7,1'-cyclopropane]-5-one (I-39);
6-[2-[1-[(5-methyl-1H-pyrrol-2-yl)methyl]-4-piperidyl]ethyl]spiro[[1,3]dioxolo[4,5-f]isoindole-7,1'-cyclopropane]-5-one (I-40);
6-[2-[1-(1H-pyrazol-5-ylmethyl)-4-piperidyl]ethyl]spiro[[1,3]dioxolo[4,5-f]isoindole-7,1'-cyclopropane]-5-one (I-41;
or a pharmaceutically acceptable salt thereof.

Among the above mentioned compounds, the preferred compound is:
6-[2-[1-(2-pyridylmethyl)-4-piperidyl]ethyl]spiro[[1,3]dioxolo[4,5-f]isoindole-7,1'-cyclopropane]-5-one (I-29) or a pharmaceutically acceptable salt thereof.

Among the above mentioned compounds, the preferred compounds are:
6-[2-[1-(2-pyridylmethyl)-4-piperidyl]ethyl]spiro[[1,3]dioxolo[4,5-f]isoindole-7,1'-cyclopropane]-5-one (I-29);
6-[2-[1-(2-pyridylmethyl)-4-piperidyl]ethyl]spiro[[1,3]dioxolo[4,5-f]isoindole-7,1'-cyclopropane]-5-one hydrochloride (I-33);
or
6-[2-[1-(2-pyridylmethyl)-4-piperidyl]ethyl]spiro[[1,3]dioxolo[4,5-f]isoindole-7,1'-cyclopropane]-5-one phosphate (I-35).

Another aspect of the present invention also relates to intermediates, i.e. the compound of formula IV and the compound of formula II, being used in the preparation of the compound of formula (I), as shown in the following formula:
the compound represented by formula IV:

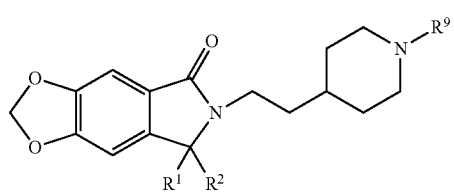

wherein:
$R^1$ and $R^2$ are as defined above; $R^9$ is an amino-protecting group, preferably tert-butoxycarbonyl (Boc);
the compound represented by formula II, or a salt thereof:

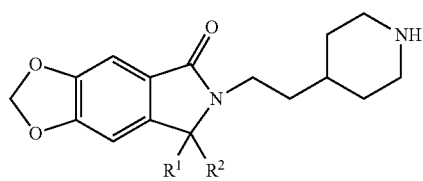

wherein:
$R^1$ and $R^2$ are as defined above.

Said salts refer to the salts formed with acids. Wherein, preferably, said acids are selected from hydrochloric acid, sulfuric acid, trifluoroacetic acid, etc.

A second aspect of the present invention discloses the use of a compound of general formula (I) and pharmaceutical compositions thereof in the preparation of a medicament for the treatment or prevention of diseases associated with inhibitors of acetylcholinesterase.

A further aspect of the present invention discloses the use of a compound of general formula (I) in the preparation of a medicament for the treatment of Alzheimer's disease.

Another aspect of the present invention focuses on a pharmaceutical composition, wherein it comprises an effective amount of the compounds according to the present invention or pharmaceutically acceptable salts thereof. The pharmaceutical composition according to the present invention can also comprises pharmaceutically acceptable carriers compatible with the compound of formula (I). The compound of formula (I) can be administered in conventional dosage forms, such as oral forms and injection forms, including capsule, tablet, powder, cachet, suspension, and solution, preferably, be administered in oral forms, more preferably, be administered in tablet and capsule, among oral forms. The dosage forms and pharmaceutical compositions can be prepared with conventional pharmaceutically acceptable excipients and additives, as well as conventional techniques. Said pharmaceutically acceptable excipients and additives include non-toxic compatible fillers, adhesives, disintegrating agents, buffers, preservatives, antioxidants, lubricants, flavoring agent, thickening agents, coloring agent, emulsifiers, etc.

A second object of the present invention is to disclose the method for preparing said benzodioxole derivatives (formula I). Said method comprises reacting a compound represented by formula II or a salt thereof with a compounds represented by formula III-1 or III-2:

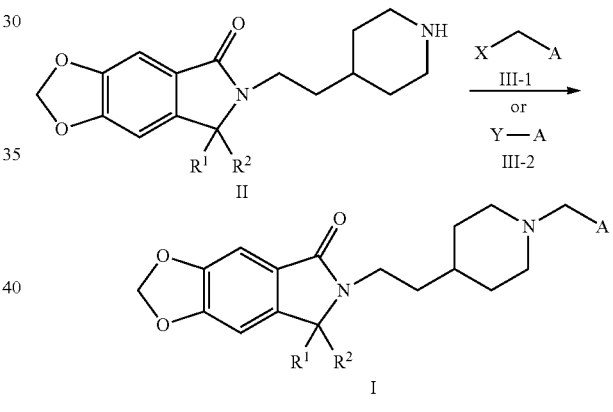

Wherein, $R^1$, $R^2$ and A are defined above; X is halogen or hydroxyl, Y is formyl or alkoxycarbonyl. When X is hydroxyl, A is pyrrolyl or substituted pyrrolyl and the reaction is carried out under basic conditions (sodium alkoxycarbonyl, potassium alkoxide, or sodium/alcohol); and when Y is alkoxycarbonyl, A is pyrrolyl or substituted pyrrolyl, and the reaction is accelerated with sodium/alcohol.

Wherein, the compound of formula II or a salt thereof can be prepared according to the following method, comprising removal of the amino-protecting group in the compound represented by formula IV:

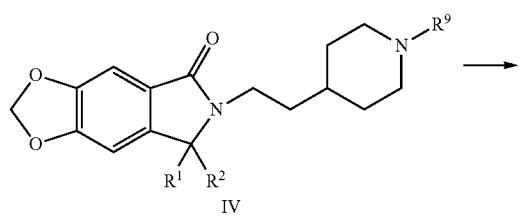

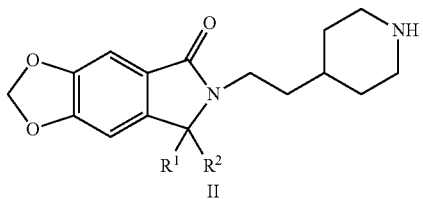

wherein, $R^1$ and $R^2$ are as defined above; $R^9$ is an amino-protecting group, preferably tert-butoxycarbonyl (Boc).

The present invention also relates to a method for forming a salt between the compound of formula (I) and an acid: i.e. mixing the compound of formula (I) and corresponding acids (such as hydrochloric acid, sulfuric acid, phosphoric acid, etc.) completely and performing after treatment, and thus corresponding salts are obtained, such as in the preparation of compound I-33, compound I-34, and compound I-35.

A third object of the present invention is to disclose the preparation of the intermediate (formula IV).

An aspect of the present invention is to provide a method for the preparation of a compound of formula (IV-1) by using compound V as the raw material (as shown in following scheme 1). This method is suitable for the compound of formula (IV) wherein $R^1$ and $R^2$ together are =O. Wherein, $R^9$ is an amino-protecting group, preferably tert-butoxycarbonyl (Boc); $R^{10}$ is halogen or tosyloxy.

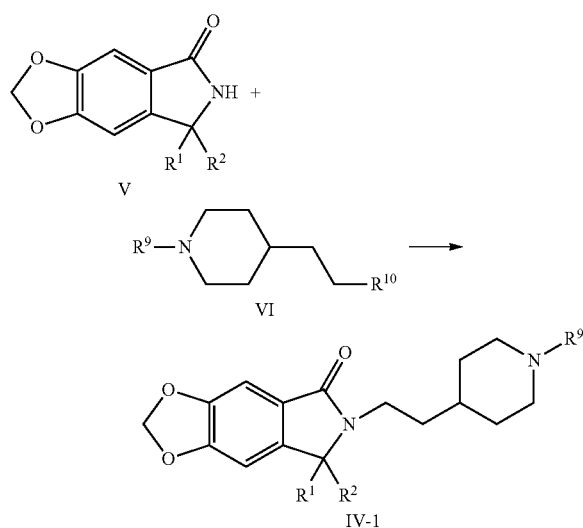

Another aspect of the present invention is to provide a method for obtaining a compound of formula (IV-2) by using compound IV-1 as the raw material, comprising: first reducing the compound represented by formula IV-1 to an alcohol, and then converting the resultant hydroxyl to an easily leavable acetoxy group, and finally removing the acetoxy group by catalytic hydrogenolysis (as shown in following Scheme 2). This method is suitable for the compound of formula (IV) wherein both $R^1$ and $R^2$ are each hydrogen. Wherein, $R^9$ is an amino-protecting group, preferably tert-butoxycarbonyl (Boc).

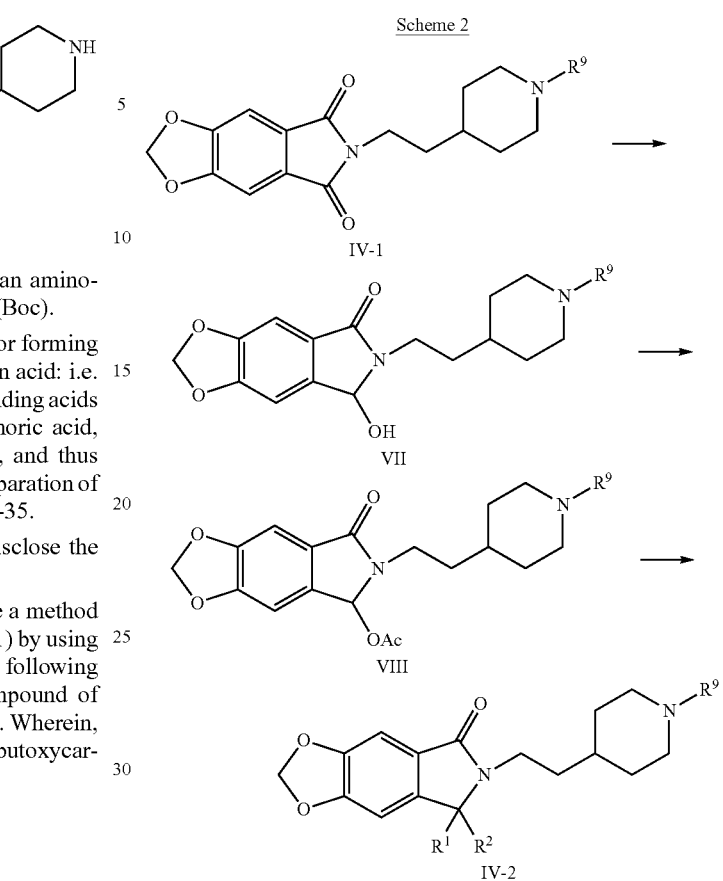

A further aspect of the present invention is to provide a method for obtaining the compound of formula (IV-3) by using compound IV-2 as the raw material and carrying out mono-alkylation at the benzyl position (i.e. the $CH_2$ group in the 5-membered lactam) of the compound represented by formula IV-2 (as shown in following Scheme 3). This method is suitable for the compound of formula (IV) wherein $R^1$ is methyl or ethyl, and $R^2$ is hydrogen. Wherein, $R^9$ is an amino-protecting group, preferably tert-butoxycarbonyl (Boc).

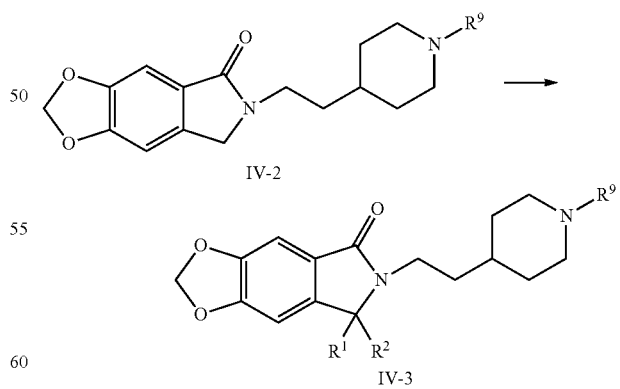

A further aspect of the present invention is to provide a method for obtaining the compound of formula (IV-4) by using compound IV-3 as the raw material and carrying out alkylation at the benzyl position (i.e. the carbon atom linked with $R^1$) of the compound represented by formula IV-3 (as shown in following Scheme 4). This method is suitable for the compound of formula (IV) wherein $R^1$ and $R^2$ are each independently methyl or ethyl. Wherein, $R^9$ is an amino-protecting group, preferably tert-butoxycarbonyl (Boc).

Scheme 4

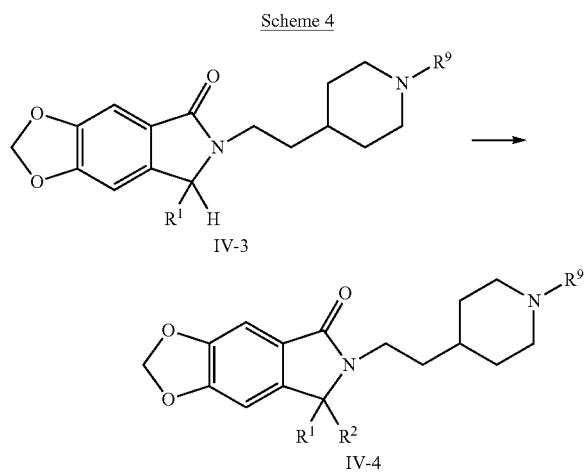

A further aspect of the present invention is to provide a method for obtaining the compound of formula (IV-5) by using compound IV-1 as the raw material and first reacting the compound represented by formula IV-1 with methyl Grignard reagent to form an alcohol, and then dehydrating the resultant alcohol to an alkene under acidic conditions, finally converting the generated carbon-carbon double bond to a 3-membered ring by using $Et_2Zn/TFA/CH_2I_2$ (as shown in the following Scheme 5). This method is suitable for the compound of formula (IV) wherein $R^1$ and $R^2$ together with the carbon atom connecting them form a 3-membered carbon ring. Wherein, $R^9$ is an amino-protecting group, preferably tert-butoxycarbonyl (Boc); and X is halogen.

Scheme 5

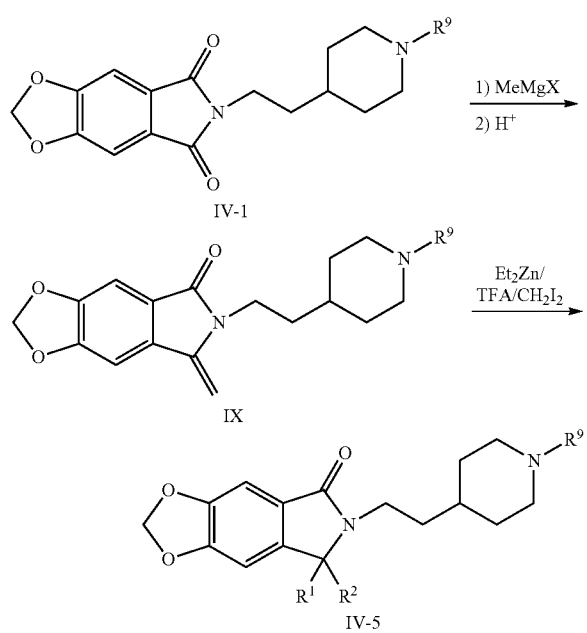

Unless otherwise indicated, the terms used in the present invention have common meanings known in the art. Further, the meanings of some terms used in the present invention are as follows:

"Halogen" refers to fluorine, chlorine, bromine, and iodine.

"Alkyl", when refers to a group, means a linear or branched saturated aliphatic hydrocarbon group. $(C_1-C_3)$ alkyl includes methyl, ethyl, n-propyl, and 2-propyl.

"Alkenyl", when refers to a group, means aliphatic hydrocarbon groups containing a carbon-carbon double bond, and can be linear or branched. $(C_2-C_3)$ alkenyl includes ethenyl, propenyl, isopropenyl, and allyl.

"Cycloalkyl" refers to saturated carbon ring. $(C_3-C_4)$ cycloalkyl includes cyclopropyl and cyclobutyl. 3-Membered ring has the same meaning as 3-membered carbon ring, and both of them refer to cyclopropyl ring, i.e., both $R^1$ and $R^2$ are $CH_2$, and are bonded by carbon-carbon single bond.

"Alkoxy" refers to group (alkyl-O—). Wherein, alkyl is as defined above. $(C_1-C_3)$ alkoxy includes methoxy, ethoxy, n-propoxy, and isopropoxy.

In addition, the term "pharmaceutically acceptable salt" refers to a certain salt of the above mentioned compound, which can keep its original biological activity and is suitable for pharmaceutical applications. A pharmaceutically acceptable salt of a compound represented by formula (I) can be a salt formed with a suitable acid, said suitable acid includes inorganic acid and organic acid, such as acetic acid, benzenesulfonic acid, benzoic acid, camphorsulfonic acid, citric acid, ethyl sulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid, p-toluenesulfonic acid, etc. Most preferred are hydrochloric acid, phosphoric acid or sulfuric acid.

The inventors have found that the compounds provided in the present invention are inhibitors of acetylcholinesterase with high activity, have significant effect of improving learning and memory, and can be used in the treatment of Alzheimer's disease.

The present invention will be further illustrated by the examples. The examples provide the preparation of representative compounds represented by formula (I) and related identification data of their structures. It should be noted that, the following examples are illustrative but not limitative.

In the following examples, unless otherwise indicated, all of the temperature refers to centigrade, and unless otherwise indicated, every raw materials and reagents are purchased from commercial source. The raw materials and reagents purchased from commercial source are used directly, without further purification, unless otherwise indicated.

The glasswares were dried by oven/or heating. The reaction was traced on a glass silica gel-60 F254 plate (0.25 mm)(TLC). Analytical thin layer chromatography was carried out, and was developed with a solvent with appropriate ratio (v/v). The end of the reaction was determined to be the exhaustion time of the raw materials on TLC.

$^1H$ NMR spectrum was determined by Bruker instrument (400 MHz), and the chemical shift was represented by ppm. Tetramethylsilane internal standard was used (0.00 ppm). The expressions in $^1H$ NMR was: s=singlet, d=doublet, t=triplet, m=multiplet, br=broad, and dd=double doublet. When coupling constant was provided, it is represented by the unit Hz.

Mass spectrum was determined by LC/MS instruments, and method of ionization can be ESI or APCI.

All of the melting points are not corrected.

The following examples are provided only for illustrating the synthesis of specific compounds according to the present invention, but are not intended to be limited to the synthesis methods. Compounds, which are not listed in the following, can also be prepared via the same synthesis schemes and synthesis methods as those provided in the following, with appropriate and well-known modification, if necessary, to reaction conditions, by choosing appropriate starting materials.

BRIEF DESCRIPTION OF THE DRAWINGS

FIG. 1 is the blood plasma drug concentration-time curve in rat after oral administration of donepezil hydrochloride, I-33, and I-35 (the abscissa is time, represented by the unit h; and the ordinate is concentration, represented by the unit nmol/L).

EXAMPLES

Example 1

Preparation of tert-butyl 4-[2-(5,7-dioxo-[1,3]dioxolo[4,5-f]isoindol-6-yl) ethyl]piperidine-1-carboxylate (compound XI)

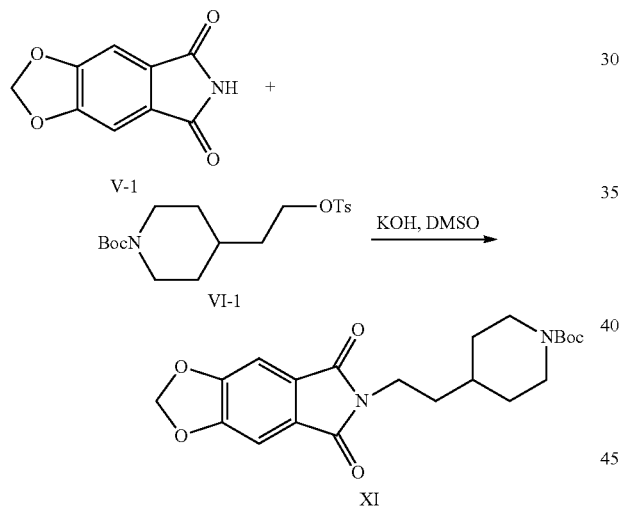

To a 1 L reaction vessel, 52 g (0.27 mol) of [1,3]dioxolo[4,5-f]isoindole-5,7-dione (compound V-1, synthesized according to the method in the references: J. Am. Chem. Soc., 1951, 73, 1371 and J. Am. Chem. Soc., 1963, 85, 473) and 320 ml dimethyl sulfoxide was added, and the mixture was stirred and heated to 60° C., 110 ml solution of 23.4 g (0.42 mol) of potassium hydroxide in ethanol was added after the solid was completely dissolved, the resulting mixture was stirred for 15 min, and then 160 ml solution of 117 g (0.31 mol) of tert-butyl 4-[2-(tosyloxy)ethyl]piperidine-1-carboxylate (compound VI-1, synthesized according to the method disclosed in the PCT application WO2007082731) in dimethyl sulfoxide was added, after addition, the reaction was kept at 60° C. for 5 h until the reaction was completed, 500 ml ethyl acetate and 300 ml water were added, extraction was carried out and the organic layer was collected, dried over sodium sulfate, filtered, the filtrate was concentrated to dry, and 102.2 g crude product was obtained, it was separated by column chromatography, and 72 g compound XI was obtained, with yield of 65.8%. $^1$H NMR (DMSO-d$_6$): δ 0.90-1.00 (m, 2H), 1.36 (s, 10H), 1.46 (q, 2H, J=7.0 Hz), 1.66 (d, 2H, J=11.9 Hz), 2.62 (br s, 2H), 3.51 (t, 2H, J=7.0 Hz), 3.88 (d, 2H, J=11.5 Hz), 6.24 (s, 2H), 7.32 (s, 2H); MS (ESI): m/z 425 [M+Na]$^+$.

Example 2

Preparation of 6-[2-(4-piperidyl)ethyl]-[1,3]dioxolo[4,5-f]isoindole-5,7-dione hydrochloride (compound II-1)

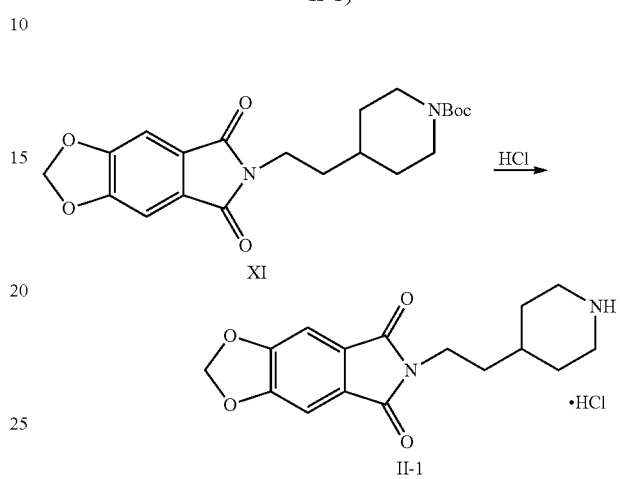

To 500 ml reaction vessel, 20 g (0.05 mol) compound XI and 400 ml 10% solution of hydrogen chloride in ethyl acetate were added, the reaction was kept at room temperature for 2 h, filtrated, washed, oven-dried, and 15.5 g compound II-1 was obtained, with yield of 92.3%. $^1$H NMR (D$_2$O): δ 1.40-1.64 (m, 5H), 2.02 (d, 2H, J=13.4 Hz), 2.96-3.03 (m, 2H), 3.45-3.50 (m, 4H), 6.12 (s, 2H), 6.79 (s, 2H); MS (ESI): m/z 303 [M−Cl]$^+$.

Example 3

Preparation of 6-[2-(1-benzyl-4-piperidyl)ethyl]-[1,3]dioxolo[4,5-f]isoindole-5,7-dione (compound I-1)

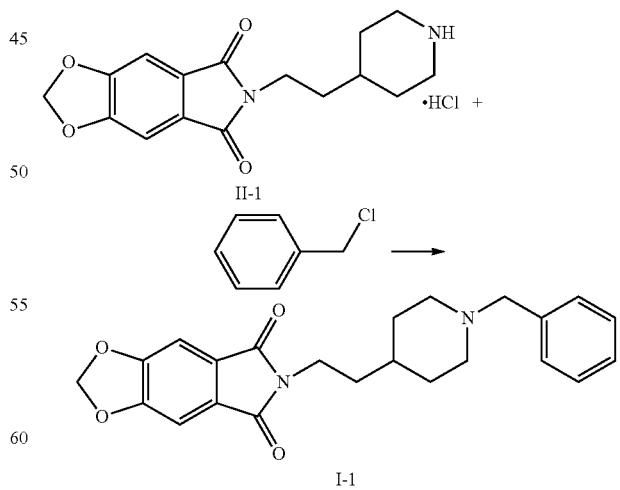

To a reaction vessel, 5 g (0.015 mol) compound II-1, 1.4 g (0.01 mol) potassium carbonate, 100 ml acetonitrile, and 2.3 ml (0.02 mol) benzyl chloride were added, the reaction was heated to 50° C. and kept for 3-4 h, 200 ml ethyl acetate and 100 ml water were added, extraction was carried out, the organic layer was collected, dried over sodium sulfate, filtrated, the filtrate was concentrated to dry, separated by column chromatography, and 3.5 g compound I-1 was obtained, with yield of 60.4%. ¹H NMR (DMSO-d₆): δ 1.08-1.17 (m, 3H), 1.48 (q, 2H, J=6.6 Hz), 1.67 (d, 2H, J=10.0 Hz), 1.85 (t, 2H, J=10.8 Hz), 2.75 (d, 2H, J=11.4 Hz), 3.41 (s, 2H), 3.53 (t, 2H, J=7.1 Hz), 6.27 (s, 2H), 7.22-7.32 (m, 5H), 7.37 (s, 2H); MS (ESI): m/z 393 [M+H]⁺.

The following compounds were prepared according to the method in example 3, by using compound II-1 as the raw material and using appropriate reagents:

To a reaction vessel, 92 g (0.23 mol) compound XI, 250 ml methanol and 250 ml tetrahydrofuran were added while stirring, the mixture was cooled to 0~10° C., 10 g (0.26 mol) sodium borohydride was added, the reaction was kept at 0~10° C. for 20-30 min, 100 ml water was added, the reaction mixture was concentrated to dry under reduced pressure (at 45° C.), The residue was added 500 ml ethyl acetate and 300 ml water, and extracted, the organic layer was collected, dried over sodium sulfate, concentrated to a minor amount, 300 ml petroleum ether was added, a solid was precipitated out, filtered, the filter cake was washed wth petroleum ether, dried, and 64.7 g compound VII-1 was obtained, with yield of 70%.

| Example | Structure | ¹H NMR (400 MHz) and MS (m/z) |
|---|---|---|
| 4 | I-2 | ¹H NMR (CDCl₃): δ 1.24-1.32 (m, 3 H), 1.58 (q, 2 H, J = 7.5 Hz), 1.75 (d, 2 H, J = 10.8 Hz), 2.00 (t, 2 H, J = 11.0 Hz), 2.89 (d, 2 H, J = 11.5 Hz), 3.57 (s, 2 H), 3.64 (t, 2 H, J = 7.4 Hz), 6.15 (s, 2 H), 6.99-7.03 (m, 1 H), 7.07-7.11 (m, 1 H), 7.19 (s, 2 H), 7.21-7.23 (m, 1 H), 7.37 (t, 1 H, J = 7.1 Hz); MS (ESI): m/z 411 [M + H]⁺. |
| 5 | I-3 | ¹H NMR (CDCl₃): δ 1.27-1.34 (m, 3 H), 1.57-1.62 (m, 2 H), 1.74 (d, 2 H, J = 9.4 Hz), 1.93 (t, 2 H, J = 10.7 Hz), 2.84 (d, 2 H, J = 11.3 Hz), 3.46 (s, 2 H), 3.65 (t, 2 H, J = 7.2 Hz), 6.15 (s, 2 H), 6.89-6.94 (m, 1 H), 7.03-7.07 (m, 2 H), 7.19 (s, 2 H), 7.21-7.27 (m, 1 H); MS (ESI): m/z 411 [M + H]⁺. |
| 6 | I-4 | ¹H NMR (DMSO-d₆): δ 1.08-1.20 (m, 3 H), 1.48 (q, 2 H, J = 6.7 Hz), 1.67 (d, 2 H, J = 10.2 Hz), 1.84 (t, 2 H, J = 11.0 Hz), 2.74 (d, 2 H, J = 11.4 Hz), 3.39 (s, 2 H), 3.53 (t, 2 H, J = 7.2 Hz), 6.27 (s, 2 H), 7.09-7.14 (m, 2 H), 7.28-7.31 (m, 2 H), 7.37 (s, 2 H); MS (ESI): m/z 411 [M + H]⁺. |

Example 7

Preparation of tert-butyl 4-[2-(5-hydroxy-7-oxo-5H-[1,3]dioxolo[4,5-f]isoindol-6-yl)ethyl]piperidine-1-carboxylate (compound VII-1)

¹H NMR (DMSO-d₆): δ 0.95-1.04 (m, 2H), 1.39 (s, 10H), 1.51 (m, 2H), 1.70 (dd, 2H, J=25.0, 12.4 Hz), 2.65 (br s, 2H), 3.23-3.30 (m, 1H), 3.54-3.61 (m, 1H), 3.90 (d, 2H, J=10.0 Hz), 5.67 (d, 1H, J=8.9 Hz), 6.12 (s, 1H), 6.13 (s, 1H), 6.50 (d, 1H, J=9.0 Hz), 7.08 (s, 1H), 7.09 (s, 1H); MS (ESI): m/z 427 [M+Na]⁺.

Example 8

Preparation of tert-butyl 4-[2-(5-acetoxy-7-oxo-5H-[1,3]dioxolo[4,5-f]isoindol-6-yl)ethyl]piperidine-1-carboxylate (compound VIII-1)

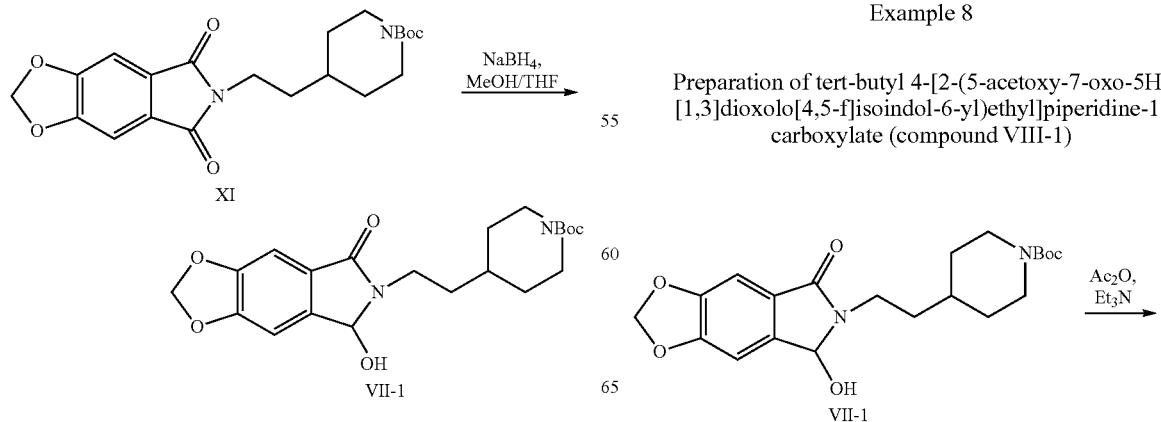

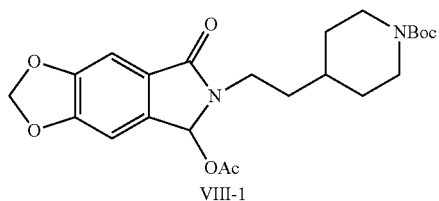

VIII-1

To a 500 ml reaction vessel, 55 g (0.136 mol) compound VII-1, 385 ml methylene dichloride, 43 ml (0.31 mol) triethylamine, and 1.8 g (0.015 mol) 4-dimethylaminopyridine were added while stirring, 31 ml (0.33 mol) acetic anhydride was added, the reaction was kept at room temperature for 1 h, 200 ml water was added, the organic layer was collected, dried over sodium sulfate, filtered, the filtrate was concentrated to dry, and about 79 g compound VIII-1 was obtained, which was used in the next step directly without further purification. $^1$H NMR (DMSO-$d_6$): δ 0.94-1.02 (m, 2H), 1.39 (s, 10H), 1.43-1.54 (m, 2H), 1.67 (t, 2H, J=9.9 Hz), 2.14 (s, 3H), 2.65 (br s, 2H), 3.17-3.24 (m, 1H), 3.56-3.64 (m, 1H), 3.90 (d, 2H, J=10.6 Hz), 6.16 (d, 1H, J=0.8 Hz), 6.18 (d, 1H, J=0.6 Hz), 6.90 (s, 1H), 7.14 (s, 1H), 7.16 (s, 1H); MS (ESI): m/z 469 [M+Na]$^+$.

Example 9

Preparation of tert-butyl 4-[2-(7-oxo-5H-[1,3]dioxolo[4,5-f]isoindol-6-yl)ethyl]piperidine-1-carboxylate (compound XII)

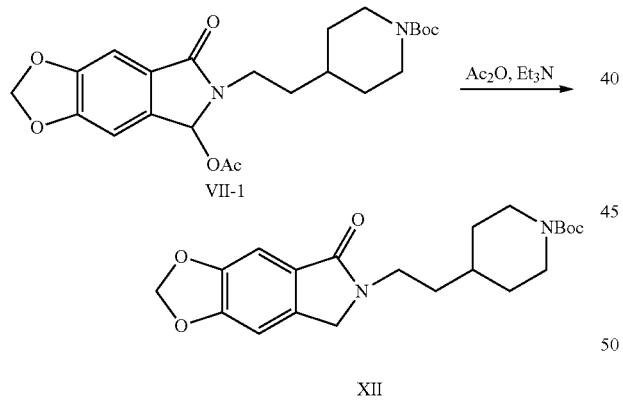

To a reaction vessel, 79 g compound VIII-1, 400 ml ethyl acetate and 17 g 5% palladium-carbon comprising 50% water were added, hydrogenation was carried out at 60° C. under normal pressure for 7-8 h until the reaction was complete, filtered, the filtrate was concentrated to a minor amount under reduced pressure, petroleum ether was added dropwise, it was cooled and a solid was precipitated out, filtered, and 33 g compound XII was obtained, with yield of about 62.5% (calculated according to compound VII-1). $^1$H NMR (DMSO-$d_6$): δ 0.94-1.04 (m, 2H), 1.39 (s, 10H), 1.47-1.54 (m, 2H), 1.69 (d, 2H, J=11.6 Hz), 2.64 (br s, 2H), 3.50 (t, 2H, J=7.0 Hz), 3.90 (d, 2H, J=11.3 Hz), 4.32 (s, 2H), 6.12 (s, 2H), 7.08 (s, 1H), 7.11 (s, 1H); MS (ESI): m/z 411 [M+Na]$^+$.

Example 10

Preparation of 6-[2-(4-piperidyl)ethyl]-5H-[1,3]dioxolo[4,5-f]isoindol-7-one hydrochloride (compound II-2)

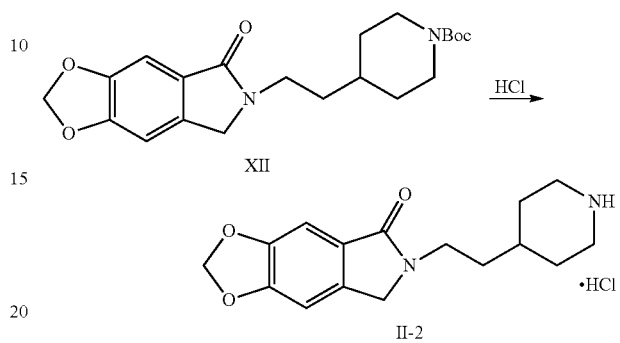

To a reaction vessel, 15 g (0.039 mol) compound XII and 300 ml 10% solution of hydrogen chloride in ethyl acetate were added, the reaction mixture was kept at room temperature for 30 min until the reaction was complete, concentrated to dry under reduced pressure, recrystallized with the mixed solution of ethanol and ethyl acetate, and 10.5 g compound II-2 was obtained, with yield of 84.3%. $^1$H NMR (D$_2$O): δ 1.38-1.49 (m, 2H), 1.59-1.61 (m, 3H), 1.98 (d, 2H, J=13.5 Hz), 2.91-2.98 (m, 2H), 3.42 (d, 2H, J=12.8 Hz), 3.49 (t, 2H, J=7.0 Hz), 4.13 (s, 2H), 5.97 (s, 2H), 6.72 (s, 1H), 6.76 (s, 1H); MS (ESI): m/z 289 [M−Cl]$^+$.

Example 11

Preparation of 6-[2-(1-benzyl-4-piperidyl)ethyl]-5H-[1,3]dioxolo[4,5-f]isoindol-7-one (compound I-5)

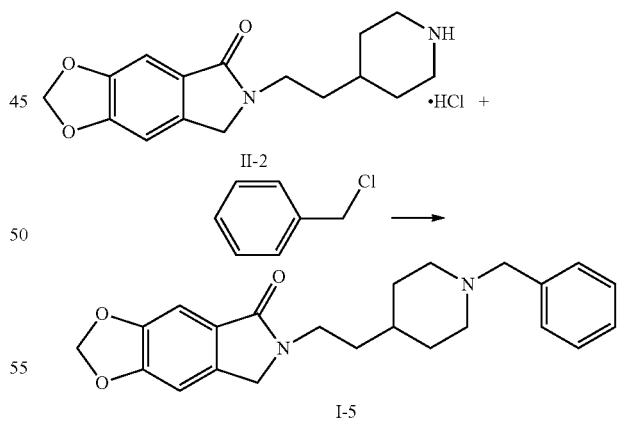

To a reaction vessel, 5 g (0.015 mol) compound II-2, 1.4 g (0.01 mol) potassium carbonate, 100 ml acetonitrile and 2.3 ml (0.02 mol) benzyl chloride were added, it was heated to 50° C. and the reaction was kept for 3-4 h until the reaction was complete, 200 ml ethyl acetate and 100 ml water were added, extracted, the organic layer was collected, dried over sodium sulfate, filtered, the filtrate was concentrated to dry, and separated by column chromatography, and 3.1 g compound I-5 was obtained, with yield of 53.4%. $^1$H NMR (CDCl₃): δ 1.26-1.36 (m, 3H), 1.57 (q, 2H, J=7.5 Hz), 1.73 (d, 2H, J=9.2 Hz), 1.93 (t, 2H, J=10.6 Hz), 2.87 (d, 2H, J=11.2 Hz), 3.48 (s, 2H), 3.60 (t, 2H, J=7.5 Hz), 4.23 (s, 2H), 6.04 (s, 2H), 6.83 (s, 1H), 7.21 (s, 1H), 7.22-7.26 (m, 1H), 7.29-7.30 (m, 4H); MS (ESI): m/z 379 [M+H]⁺.

The following compounds were prepared according to the method in example 11, by using compound II-2 as the raw material and using appropriate reagents:

were added, extracted, the organic layer was collected, dried over sodium sulfate, filtered, the filtrate was concentrated to dry under reduced pressure, separated by column chromatography, and 14.5 g compound XIII was obtained, with yield of 46.7%. ¹H NMR (CDCl₃): δ 1.07-1.21 (m, 2H), 1.41 (d, 3H, J=6.7 Hz), 1.45 (s, 10H), 1.55 (q, 2H, J=7.4 Hz), 1.66-1.69 (m, 1H), 1.80-1.83 (m, 1H), 2.64-2.71 (m, 2H), 3.17-3.24 (m,

| Example | Structure | ¹H NMR (400 MHz) and MS (m/z) |
|---|---|---|
| 12 | I-6 | ¹H NMR (CDCl₃): δ 1.29-1.34 (m, 3 H), 1.57 (q, 2 H, J = 5.4 Hz), 1.74 (d, 2 H, J = 8.8 Hz), 1.99 (t, 2 H, J = 10.2 Hz), 2.88 (d, 2 H, J = 10.7 Hz), 3.56 (s, 2 H), 3.59 (t, 2 H, J = 7.2 Hz), 4.22 (s, 2 H), 6.03 (s, 2 H), 6.82 (s, 1 H), 7.00 (t, 1 H, J = 9.2 Hz), 7.08 (t, 1 H, J = 7.3 Hz), 7.20-7.22 (m, 2 H), 7.35 (t, 1 H, J = 7.1 Hz); MS (ESI)): m/z 397 [M + H] ⁺. |
| 13 | I-7 | ¹H NMR (DMSO-d₆): δ 1.12-1.17 (m, 3 H), 1.50 (q, 2 H, J = 5.4 Hz), 1.68 (d, 2 H, J = 8.5 Hz), 1.87 (t, 2 H, J = 9.4 Hz), 2.75 (d, 2 H, J = 10.6 Hz), 3.43 (s, 2 H), 3.49 (t, 2 H, J = 7.1 Hz), 4.31 (s, 2 H), 6.12 (s, 2 H), 7.03-7.12 (m, 5 H), 7.32-7.37 (m, 1 H); MS (ESI): m/z 397 [M + H] ⁺. |
| 14 | I-8 | ¹H NMR (CDCl₃): δ 1.26-1.32 (m, 3 H), 1.57 (q, 2 H, J = 5.0 Hz), 1.72-1.74 (m, 2 H), 1.92 (t, 2 H, J = 10.6 Hz), 2.83 (d, 2 H, J = 10.9 Hz), 3.43 (s, 2 H), 3.60 (t, 2 H, J = 7.4 Hz), 4.23 (s, 2 H), 6.04 (s, 2 H), 6.83 (s, 1 H), 6.96-7.00 (m, 2 H), 7.21 (s, 1 H), 7.24-7.27 (m, 2 H); MS (ESI): m/z 397 [M + H] ⁺. |

Example 15

Preparation of tert-butyl 4-[2-(5-methyl-7-oxo-5H-[1,3]dioxolo[4,5-f]isoindol-6-yl)ethyl]piperidine-1-carboxylate (compound XIII)

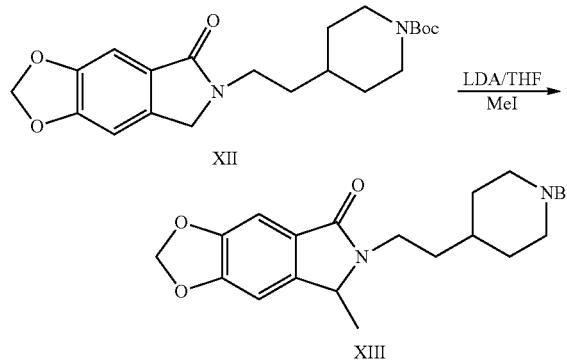

To a reaction vessel, 30 g (0.077 mol) compound XII and 300 ml tetrahydrofuran were added under nitrogen, the mixture was cooled to −10−−15° C., 78 ml (0.16 mol, 2 mol/L) solution of lithium diisopropylamide in n-heptane was added dropwise for about 30 min, after the addition was complete, the reaction was kept at this temperature for 30 min, 4.8 ml (0.077 mol) iodomethane was added dropwise, after the addition was complete, the mixture was warmed to room temperature and stirred for 2 h, 600 ml ethyl acetate and 300 ml water 1H), 3.92-4.00 (m, 1H), 4.06-4.09 (m, 2H), 4.41 (q, 1H, J=6.7 Hz), 6.05 (s, 2H), 6.82 (s, 1H), 7.20 (s, 1H); MS (ESI): m/z 403 [M+H]⁺.

Example 16

Preparation of 5-methyl-6-[2-(4-piperidyl)ethyl]-5H-[1,3]dioxolo[4,5-f]isoindol-7-one hydrochloride (compound II-3)

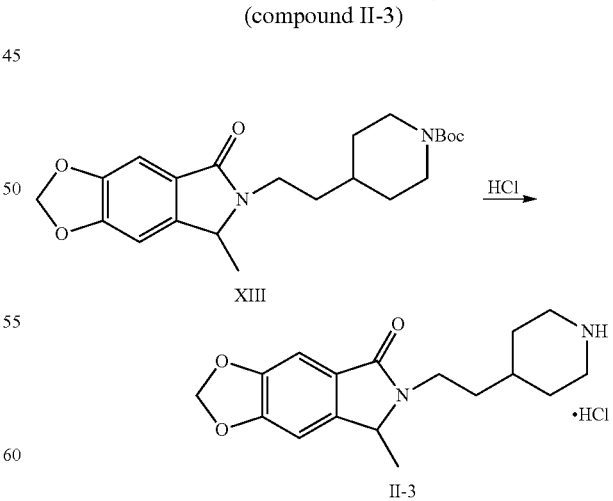

To a reaction vessel, 5 g (0.012 mol) compound XIII, 30 ml ethanol and 100 ml 10% solution of hydrogen chloride in ethyl acetate were added, the reaction was kept at room temperature for 1-1.5 h, filtered, the filter cake was washed with ethyl acetate, dried, and 3.4 g compound II-3 was obtained, with yield of 81%. ¹H NMR (D₂O): δ 1.24 (d, 3H, J=7.0 Hz), 1.44-1.58 (m, 5H), 1.98 (m, 2H), 2.96 (m, 2H), 3.21-3.25 (m, 1H), 3.44 (d, 2H, J=12.4 Hz), 3.64-3.72 (m, 1H), 4.34 (q, 1H, J=6.6 Hz), 5.94 (s, 2H), 6.72 (s, 1H), 6.79 (s, 1H); MS (ESI): m/z 303 [M+H]⁺.

Example 17

Preparation of 6-[2-(1-benzyl-4-piperidyl) ethyl]-5-methyl-5H-[1,3]dioxolo[4,5-f]isoindol-7-one (compound I-9)

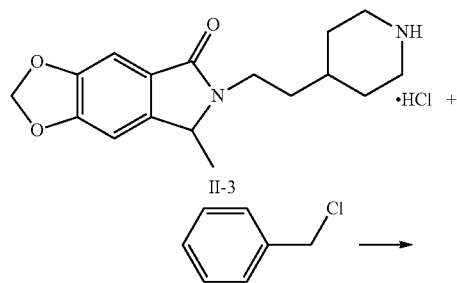

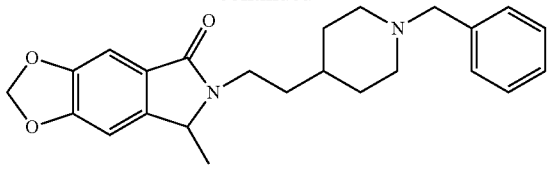

I-9

To a reaction vessel, 2 g (0.006 mol) compound II-3 and 40 ml acetonitrile were added, stirred, 2.4 g (0.017 mol) potassium carbonate, 1.2 ml (0.0087 mol) triethylamine, and 1.5 ml (0.013 mol) benzyl chloride were added. The mixture was heated to 50° C., the reaction was kept for 1.5 h, 200 ml ethyl acetate and 100 ml water were added, extracted, the organic layer was collected, dried over sodium sulfate, filtered, the filtrate was concentrated to dry, separated by column chromatography, and 1.1 g compound I-9 was obtained, with yield of 47.4%. ¹H NMR (CDCl₃): δ 1.34-1.42 (m, 3H), 1.46 (d, 3H, J=6.7 Hz), 1.59-1.64 (m, 2H), 1.72-1.75 (m, 1H), 1.86-1.89 (m, 1H), 1.97-2.04 (m, 2H), 2.94 (t, 2H, J=9.1 Hz), 3.21-3.28 (m, 1H), 3.55 (s, 2H), 3.97-4.05 (m, 1H), 4.46 (q, 1H, J=6.7 Hz), 6.09 (s, 2H), 6.87 (s, 1H), 7.26 (s, 1H), 7.29-7.32 (m, 1H), 7.34-7.37 (m, 4H); MS (ESI): m/z 393 [M+H]⁺.

The following compounds were prepared according to the method in example 17, by using compound II-3 as the raw material and using appropriate reagents:

| Example | Structure | ¹H NMR (400 MHz) and MS (m/z) |
| --- | --- | --- |
| 18 | I-10 | ¹H NMR (CDCl₃): δ 1.36-1.42 (m, 3 H), 1.46 (d, 3 H, J = 6.7 Hz), 1.58-1.63 (m, 2 H), 1.73-1.76 (m, 1 H), 1.87-1.89 (m, 1 H), 2.05-2.10 (m, 2 H), 2.95 (m, 2 H), 3.20-3.27 (m, 1 H), 3.63 (s, 2 H), 3.98-4.05 (m, 1 H), 4.46 (q, 1 H, J = 6.6 Hz), 6.10 (s, 2 H), 6.87 (s, 1 H), 7.07 (t, 1 H, J = 9.1 Hz), 7.16 (t, 1 H, J = 7.4 Hz), 7.26-7.35 (m, 2 H), 7.43 (t, 1 H, J = 7.1 Hz); MS (ESI): m/z 411 [M + H]⁺. |
| 19 | I-11 | ¹H NMR (CDCl₃): δ 1.34-1.42 (m, 3 H), 1.46 (d, 3 H, J = 6.8 Hz), 1.59-1.64 (m, 2 H), 1.72-1.75 (m, 1 H), 1.87-1.89 (m, 1 H), 1.99-2.04 (m, 2 H), 2.92 (t, 2 H, J = 8.9 Hz), 3.21-3.28 (m, 1 H), 3.54 (s, 2 H), 3.97-4.05 (m, 1 H), 4.47 (q, 1 H, J = 6.7 Hz), 6.10 (s, 2 H), 6.88 (s, 1 H), 6.96-7.01 (m, 1 H), 7.10-7.15 (m, 2 H), 7.26 (s, 1 H), 7.30-7.34 (m, 1 H); MS (ESI): m/z 411 [M + H]⁺. |
| 20 | I-12 | ¹H NMR (CDCl₃): δ 1.32-1.40 (m, 3 H), 1.46 (d, 3 H, J = 6.7 Hz), 1.59-1.64 (m, 2 H), 1.73-1.75 (m, 1 H), 1.86-1.88 (m, 1 H), 1.95-2.00 (m, 2 H), 2.90 (t, 2 H, J = 8.2 Hz), 3.21-3.28 (m, 1 H), 3.50 (s, 2 H), 3.98-4.05 (m, 1 H), 4.47 (q, 1 H, J = 6.7 Hz), 6.10 (s, 2 H), 6.88 (s, 1 H), 7.02-7.06 (m, 2 H), 7.26 (s, 1 H), 7.31-7.34 (m, 2 H); MS (ESI): m/z 411 [M + H]⁺. |

Example 21

Preparation of tert-butyl 4-[2-(7,7-dimethyl-5-oxo-[1,3]dioxolo[4,5-f]isoindol-6-yl)ethyl]piperidine-1-carboxylate (compound XIV)

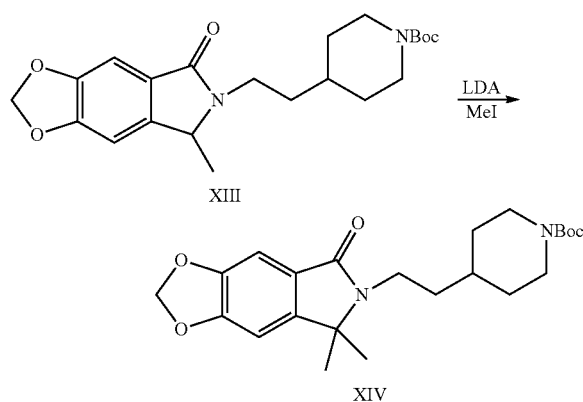

To a reaction vessel, 10 g (0.025 mol) compound XIII and 100 ml tetrahydrofuran were added, stirred, under nitrogen, the mixture was cooled to −10~−15° C., 48 ml (0.096 mol, 2 mol/L) solution of lithium diisopropylamide in n-heptane was added dropwise for about 30 min, after the addition was complete, the reaction was kept for 30 min, and then 1.6 ml (0.026 mol) iodomethane was added dropwise, after the addition was complete, the mixture was warmed to room temperature and then stirred for 1 h, after the reaction was complete, 300 ml ethyl acetate and 150 ml water were added, extracted and washed, the organic layer was collected, dried over sodium sulfate, filtered, the filtrate was concentrated to dry under reduced pressure, separated by column chromatography, and 5.6 g compound XIV was obtained, with yield of 54.2%. MS (ESI): m/z 417 [M+H]$^+$.

Example 22

Preparation of 7,7-dimethyl-6-[2-(4-piperidyl)ethyl]-[1,3]dioxolo[4,5-f]isoindol-5-one hydrochloride (compound II-4)

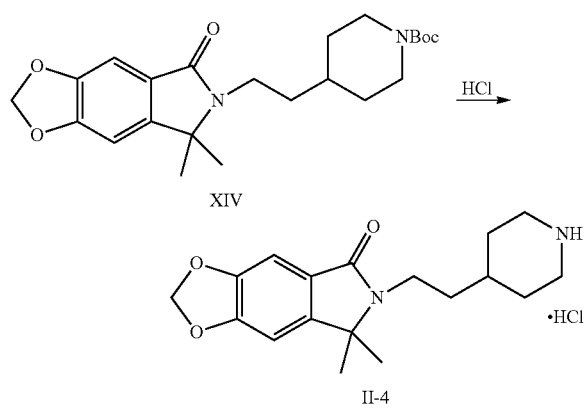

To a reaction vessel, 2 g (0.0048 mol) compound XIV, 10 ml ethanol and 50 ml 10% solution of hydrogen chloride in ethyl acetate were added, the reaction was kept at room temperature for 1-1.5 h, filtrated, the filter cake was washed with ethyl acetate, dried, and 1.2 g compound II-4 was obtained, with yield of 71%. $^1$H NMR (D$_2$O): δ 1.27 (s, 6H), 1.45 (m, 2H), 1.56 (q, 2H, J=6.9 Hz), 1.69 (br s, 1H), 2.00 (d, 2H, J=13.9 Hz), 3.00 (t, 2H, J=12.6 Hz), 3.37 (t, 2H, J=7.6 Hz), 3.45 (d, 2H, J=12.3 Hz), 5.96 (s, 2H), 6.79 (s, 1H), 6.86 (s, 1H); MS (ESI): m/z 317 [M-Cl]$^+$.

Example 23

Preparation of 6-[2-(1-benzyl-4-piperidyl) ethyl]-7,7-dimethyl-[1,3]dioxolo[4,5-f]isoindol-5-one (compound I-13)

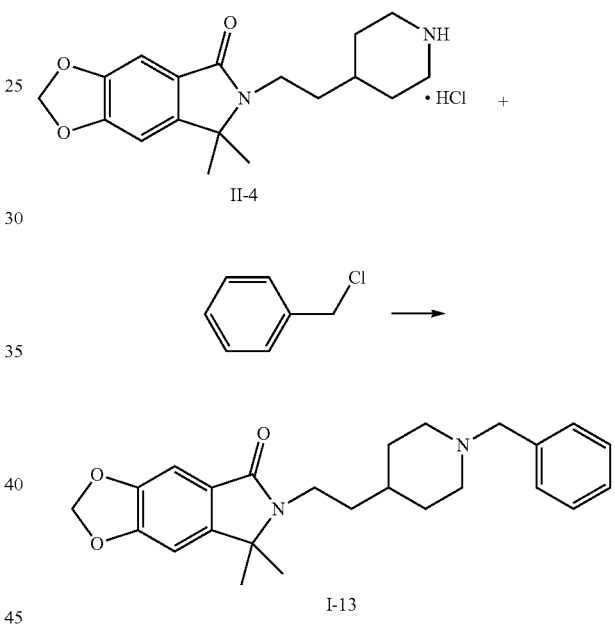

To a reaction vessel, 2.3 g (0.0065 mol) compound II-4 and 46 ml acetonitrile were added while stirring. 6 g (0.043 mol) potassium carbonate, 1.3 ml (0.0094 mol) triethylamine, and 1.7 ml (0.015 mol) benzyl chloride were added, the mixture was heated to 50° C., the reaction was kept for 2-3 h, 200 ml ethyl acetate and 100 ml water were added, extracted and washed, the organic layer was collected, dried over sodium sulfate, filtered, the filtrate was concentrated to dry, separated by column chromatography, and 1.8 g compound I-13 was obtained, with yield of 67.7%. $^1$H NMR (DMSO-d$_6$): δ 1.18-1.23 (m, 2 H), 1.26-1.33 (m, 1H), 1.40 (s, 6H), 1.50-1.56 (m, 2H), 1.70 (d, 2H, J=11.2 Hz), 1.89 (t, 2H, J=10.4 Hz), 2.77 (d, 2H, J=11.2 Hz), 3.35 (t, 2H, J=7.8 Hz), 3.42 (s, 2H), 6.12 (s, 2H), 7.05 (s, 1H), 7.21-7.25 (m, 2H), 7.27-7.33 (m, 4H); MS (ESI): m/z 407 [M+H]$^+$.

The following compounds were prepared according to the method in example 23, by using compound II-4 as the raw material and using appropriate reagents:

| Example | structure | ¹H NMR (400 MHz) and MS (m/z) |
|---|---|---|
| 24 | I-14 | ¹H NMR (DMSO-d₆): δ 1.13-1.22 (m, 2 H), 1.23-1.28 (m, 1 H), 1.39 (s, 6 H), 1.48-1.54 (m, 2 H), 1.70 (d, 2 H, J = 11.6 Hz), 1.94 (t, 2 H, J = 10.9 Hz), 2.78 (d, 2 H, J = 11.2 Hz), 3.33 (t, 2 H, J = 7.7 Hz), 3.48 (s, 2 H), 6.10 (s, 2 H), 7.03 (s, 1 H), 7.12-7.18 (m, 2 H), 7.24 (s, 1 H), 7.27-7.32 (m, 1 H), 7.39 (t, 1 H, J = 7.4 Hz); MS (ESI): m/z 425 [M + H]⁺. |
| 25 | I-15 | ¹H NMR (DMSO-d₆): δ 1.15-1.24 (m, 2 H), 1.25-1.31 (m, 1 H), 1.40 (s, 6 H), 1.50-1.55 (m, 2 H), 1.71 (d, 2 H, J = 10.8 Hz), 1.91 (t, 2 H, J = 11.2 Hz), 2.77 (d, 2 H, J = 11.5 Hz), 3.35 (t, 2 H, J = 8.2 Hz), 3.45 (s, 2 H), 6.11 (s, 2 H), 7.03-7.14 (m, 4 H), 7.25 (s, 1 H), 7.32-7.38 (m, 1 H); MS (ESI): m/z 425 [M + H]⁺. |
| 26 | I-16 | ¹H NMR (DMSO-d₆): δ 1.13-1.22 (m, 2 H), 1.25-1.29 (m, 1 H), 1.41 (s, 6 H), 1.50-1.55 (m, 2 H), 1.70 (d, 2 H, J = 11.2 Hz), 1.89 (t, 2 H, J = 10.7 Hz), 2.76 (d, 2 H, J = 11.2 Hz), 3.35 (t, 2 H, J = 7.7 Hz), 3.40 (s, 2 H), 6.12 (s, 2 H), 7.04 (s, 1 H), 7.12 (t, 2 H, J = 8.9 Hz), 7.25 (s, 1 H), 7.29-7.33 (m, 2 H); MS (ESI): m/z 425 [M + H]⁺. |

Example 27

Preparation of tert-butyl 4-[2-(5-methylene-7-oxo-[1,3]dioxolo[4,5-f]isoindol-6-yl)ethyl]piperidine-1-carboxylate (compound IX-1)

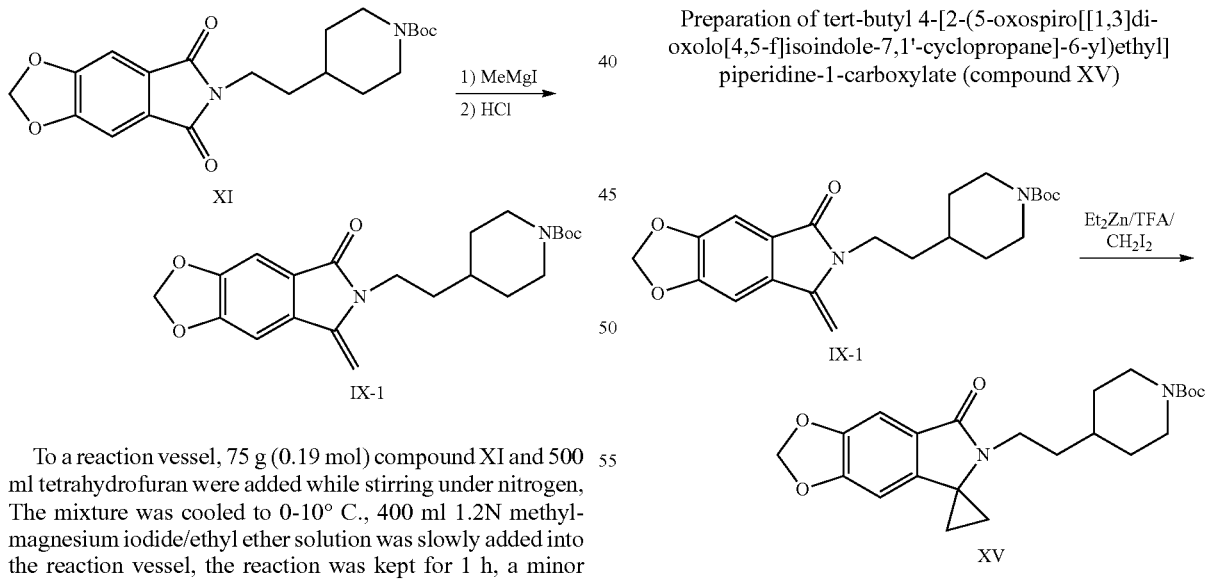

To a reaction vessel, 75 g (0.19 mol) compound XI and 500 ml tetrahydrofuran were added while stirring under nitrogen, The mixture was cooled to 0-10° C., 400 ml 1.2N methylmagnesium iodide/ethyl ether solution was slowly added into the reaction vessel, the reaction was kept for 1 h, a minor amount of water was added until there was no bubble formed, concentrated hydrochloric acid was added to adjust the pH to acidic, the reaction was kept for 15 min, 500 ml ethyl acetate and 300 ml water were added, extracted, washed, the organic layer was collected, dried over sodium sulfate, filtered, the filtrate was concentrated to a minor amount, petroleum ether was added, solid was precipitated out, filtered, dried, and 47.6 g compound IX-1 was obtained, with yield of 63.8%. ¹H NMR (DMSO-d₆): δ 0.95-1.05 (m, 2H), 1.38 (s, 10H), 1.48 (q, 2H, J=7.0 Hz), 1.71 (d, 2H, J=12.2 Hz), 2.65 (br s, 2H), 3.70 (t, 2H, J=7.2 Hz), 3.90 (d, 2H, J=11.6 Hz), 4.95 (s, 1H), 5.34 (s, 1H), 6.17 (s, 2H), 7.15 (s, 1H), 7.53 (s, 1H); MS (ESI): m/z 423 [M+Na]⁺.

Example 28

Preparation of tert-butyl 4-[2-(5-oxospiro[[1,3]dioxolo[4,5-f]isoindole-7,1'-cyclopropane]-6-yl)ethyl]piperidine-1-carboxylate (compound XV)

To a reaction vessel, 300 ml methylene dichloride and 300 ml (1N) solution of diethylzinc in hexane were added under nitrogen, The mixture was cooled to 0-10° C., 200 ml solution containing 23.1 ml (0.31 mol) trifluoroacetic acid in methylene dichloride was added dropwise for about 20 min, after the addition was complete, the reaction was kept for 20 min, 200 ml solution containing 24 ml (0.3 mol) methylene diiodide in methylene dichloride was added dropwise, after the addition was complete, the reaction was kept for 20 min, and then 300 ml solution of 60 g (0.15 mol) compound IX-1 in methylene dichloride was added dropwise, after the addition was complete, the mixture was heated to 30° C., the reaction was kept for 3-4 h, 500 ml water was added, the pH was adjusted to neutral with 1N hydrogen chloride, the layers was separated, the organic layer was collected, dried over sodium sulfate, filtered, the filtrate was concentrated to dry under reduced pressure, and compound XV was obtained, it was subjected to the next reaction directly. $^1$H NMR (CDCl$_3$): δ 1.08-1.19 (m, 2H), 1.28 (dd, 2H, J=6.2, 7.4 Hz), 1.45 (s, 9H), 1.48-1.57 (m, 5H), 1.72 (d, 2H, J=12.7 Hz), 2.69 (t, 2H, J=11.6 Hz), 3.20 (t, 2H, J=7.6 Hz), 4.07 (d, 2H, J=13.1 Hz), 6.03 (s, 2H), 6.43 (s, 1H), 7.23 (s, 1H); MS (ESI): m/z 437 [M+Na]$^+$.

Example 29

Preparation of 6-[2-(4-piperidyl)ethyl]spiro[[1,3]dioxolo[4,5-f]isoindole-7,1'-cyclopropane]-5-one hydrochloride (compound II-5)

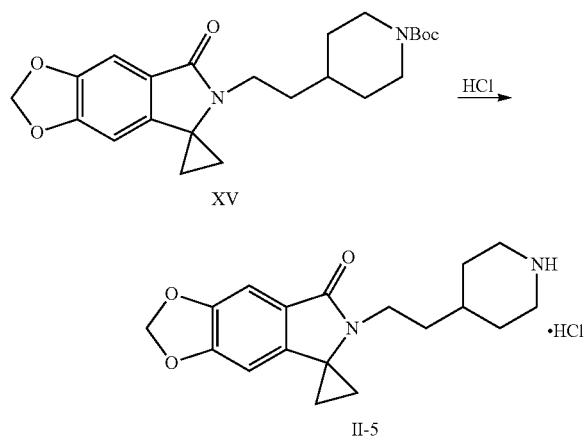

To a reaction vessel, all compound XV obtained in the above step and 750 ml ethanol were added. The mixture was heated until dissolved completely, 36 ml concentrated hydrochloric acid was added, the reaction was kept at about 50-55° C. for 5 h, concentrated to about 200 ml under reduced pressure, 900 ml ethyl acetate was added dropwise, cooled and filtered, the filter cake was washed and dried, and 24.3 g compound II-5 was obtained, with yield of 46.2% (calculated according to compound IX-1). $^1$H NMR (D$_2$O): δ 1.06 (t, 2H, J=6.7 Hz), 1.32-1.46 (m, 6H), 1.60 (m, 1H), 1.91 (d, 2H, J=13.5 Hz), 2.91-3.03 (m, 4H), 3.39 (d, 2H, J=12.8 Hz), 5.90 (s, 2H), 6.18 (s, 1H), 6.68 (s, 1H); MS (ESI): m/z 315 [M-Cl]$^+$.

Example 30

Preparation of 6-[2-(1-benzyl-4-piperidyl)ethyl]spiro[[1,3]dioxolo[4,5-f]isoindole-7,1'-cyclopropane]-5-one (compound I-17)

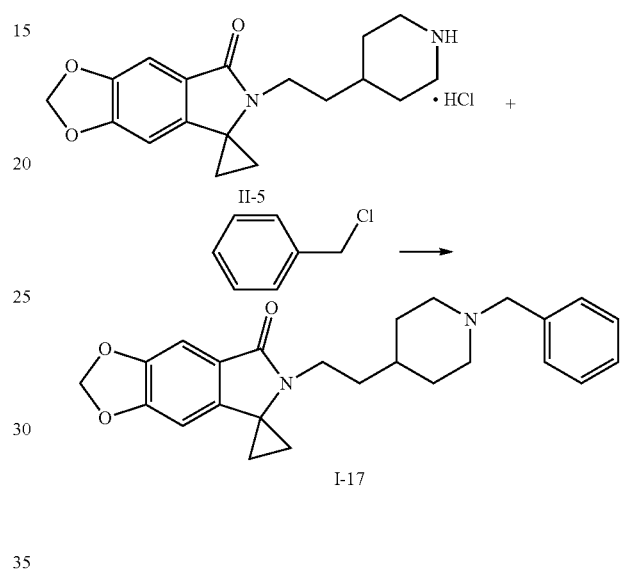

To a reaction vessel, 2 g (0.006 mol) compound II-5 and 40 ml acetonitrile were added while stirring, 1.2 g (0.008 mol) potassium carbonate, 1 ml (0.007 mol) triethylamine, and 2 ml (0.017 mol) benzyl chloride were added. The mixture was heated to 60° C., the reaction was kept for 2.5 h, 200 ml ethyl acetate and 100 ml water were added, extracted, washed, the organic layer was collected, dried over sodium sulfate, filtered, the filtrate was concentrated to dry, separated by column chromatography, and 1.5 g compound I-17 was obtained, with yield of 65.2%. $^1$H NMR (CDCl$_3$): δ 1.24-1.33 (m, 5H), 1.49-1.57 (m, 4H), 1.72 (d, 2H, J=9.6 Hz), 1.96 (t, 2H, J=10.8 Hz), 2.87 (d, 2H, J=11.4 Hz), 3.19 (t, 2H, J=7.8 Hz), 3.49 (s, 2H), 6.03 (s, 2H), 6.42 (s, 1H), 7.22-7.25 (m, 2H), 7.28-7.32 (m, 4H); MS (ESI): m/z 405 [M+H]$^+$.

The following compounds were prepared according to the method in example 30, by using compound II-5 as the raw material and using appropriate reagents:

| Example | structure | $^1$H NMR (400 MHz) and MS (m/z) |
|---|---|---|
| 31 | I-18 | $^1$H NMR (CDCl$_3$): δ 1.23-1.31 (m, 5 H), 1.48-1.55 (m, 4 H), 1.72 (d, 2 H, J = 9.2 Hz), 2.02 (t, 2 H, J = 10.3 Hz), 2.88 (d, 2 H, J = 11.2 Hz), 3.18 (t, 2 H, J = 7.9 Hz), 3.56 (s, 2 H), 6.02 (s, 2 H), 6.41 (s, 1 H), 6.99-7.03 (m, 1 H), 7.07-7.11 (m, 1 H), 7.19-7.25 (m, 2 H), 7.35-7.39 (m, 1 H); MS (ESI): m/z 423 [M + H]$^+$. |

| Example | structure | ¹H NMR (400 MHz) and MS (m/z) |
|---|---|---|
| 32 | 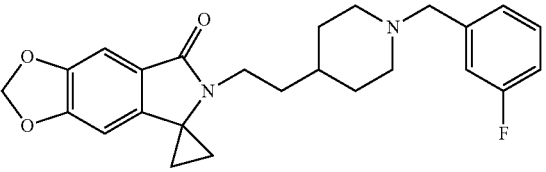<br>I-19 | ¹H NMR (CDCl₃): δ 1.24-1.32 (m, 5 H), 1.49-1.56 (m, 4 H), 1.71 (d, 2 H, J = 10.2 Hz), 1.95 (t, 2 H, J = 10.7 Hz), 2.83 (d, 2 H, J = 11.2 Hz), 3.19 (t, 2 H, J = 7.7 Hz), 3.45 (s, 2 H), 6.02 (s, 2 H), 6.41 (s, 1 H), 6.89-6.93 (m, 1 H), 7.03-7.07 (m, 2 H), 7.21-7.27 (m, 2 H); MS (ESI): m/z 423 [M + H] ⁺. |
| 33 | 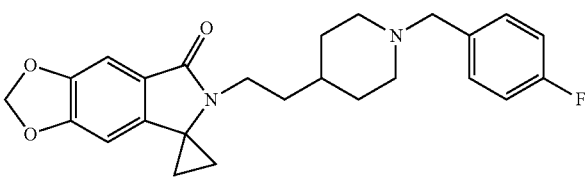<br>I-20 | ¹H NMR (CDCl₃): δ 1.24-1.32 (m, 5 H), 1.49-1.56 (m, 4 H), 1.72 (d, 2 H, J = 10.2 Hz), 1.94 (t, 2 H, J = 10.7 Hz), 2.84 (d, 2 H, J = 11.4 Hz), 3.18 (t, 2 H, J = 7.9 Hz), 3.44 (s, 2 H), 6.02 (s, 2 H), 6.42 (s, 1 H), 6.95-7.01 (m, 2 H), 7.24 (s, 1 H), 7.25-7.28 (m, 2 H); MS (ESI): m/z 423 [M + H] ⁺. |
| 34 | 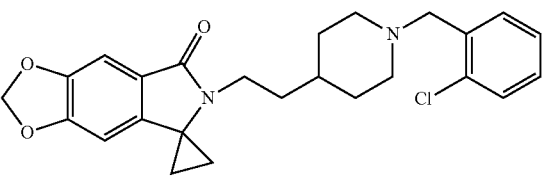<br>I-21 | ¹H NMR (CDCl₃): δ 1.26-1.36 (m, 5 H), 1.52-1.59 (m, 4 H), 1.75 (d, 2 H, J = 9.9 Hz), 2.09 (t, 2 H, J = 10.3 Hz), 2.91 (d, 2 H, J = 11.2 Hz), 3.21 (t, 2 H, J = 7.9 Hz), 3.61 (s, 2 H), 6.05 (s, 2 H), 6.44 (s, 1 H), 7.16-7.21 (m, 1 H), 7.23-7.29 (m, 2 H), 7.35 (dd, 1 H, J = 7.8, 1.1 Hz), 7.50 (d, 1 H, J = 7.1 Hz); MS (ESI): m/z 439 [M + H] ⁺. |
| 35 | 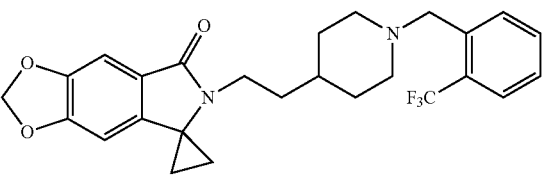<br>I-22 | ¹H NMR (CDCl₃): δ 1.24-1.34 (m, 5 H), 1.50-1.58 (m, 4 H), 1.72 (d, 2 H, J = 10.2 Hz), 2.04 (t, 2 H, J = 10.8 Hz), 2.83 (d, 2 H, J = 11.3 Hz), 3.19 (t, 2 H, J = 7.9 Hz), 3.62 (s, 2 H), 6.02 (s, 2 H), 6.42 (s, 1 H), 7.24 (s, 1 H), 7.30 (t, 1 H, J = 7.6 Hz), 7.50 (t, 1 H, J = 7.5 Hz), 7.60 (d, 1 H, J = 7.9 Hz), 7.80 (d, 1 H, J = 7.7 Hz); MS (ESI): m/z 473 [M + H] ⁺. |
| 36 | 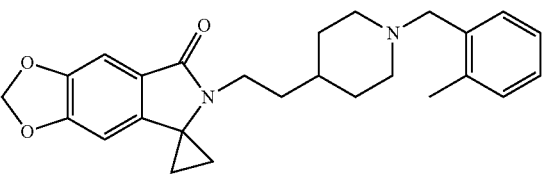<br>I-23 | ¹H NMR (CDCl₃): δ 1.26-1.37 (m, 5 H), 1.51-1.58 (m, 4 H), 1.71 (d, 2 H, J = 11.8 Hz), 1.99 (t, 2 H, J = 11.0 Hz), 2.37 (s, 3 H), 2.87 (d, 2 H, J = 11.0 Hz), 3.21 (t, 2 H, J = 7.6 Hz), 3.43 (s, 2 H), 6.04 (s, 2 H), 6.44 (s, 1 H), 7.16 (s, 3 H), 7.26-7.29 (m, 2 H); MS (ESI): m/z 419 [M + H] ⁺. |
| 37 | 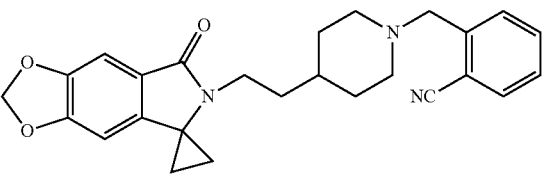<br>I-24 | ¹H NMR (CDCl₃): δ 1.25-1.33 (m, 5 H), 1.49-1.57 (m, 4 H), 1.72 (d, 2 H, J = 10.7 Hz), 2.09 (t, 2 H, J = 10.8 Hz), 2.85 (d, 2 H, J = 11.1 Hz), 3.19 (t, 2 H, J = 7.8 Hz), 3.67 (s, 2 H), 6.03 (s, 2 H), 6.42 (s, 1 H), 7.23 (s, 1 H), 7.31-7.35 (m, 1 H), 7.52-7.55 (m, 2 H), 7.62 (d, 1 H, J = 7.7 Hz); MS (ESI): m/z 430 [M + H] ⁺. |
| 38 | 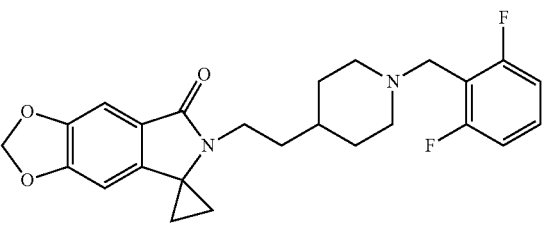<br>I-25 | ¹H NMR (CDCl₃): δ 1.24-1.27 (m, 5 H), 1.49-1.51 (m, 4 H), 1.71 (d, 2 H, J = 9.0 Hz), 2.04 (t, 2 H, J = 10.4 Hz), 2.91 (d, 2 H, J = 10.4 Hz), 3.17 (t, 2 H, J = 7.8 Hz), 3.68 (s, 2 H), 6.02 (s, 2 H), 6.41 (s, 1 H), 6.87 (t, 2 H, J = 7.5 Hz), 7.22 (m, 2 H); MS (ESI): m/z 441 [M + H] ⁺. |

| Example | structure | ¹H NMR (400 MHz) and MS (m/z) |
|---|---|---|
| 39 | 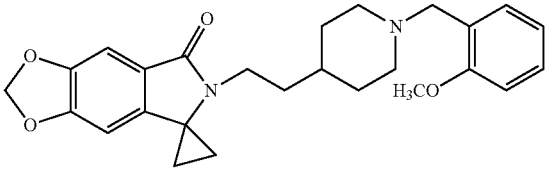<br>I-26 | ¹H NMR (DMSO-d₆): δ 1.14-1.24 (m, 3 H), 1.33 (t, 2 H, J = 7.2 Hz), 1.40 (q, 2 H, J = 6.5 Hz), 1.57 (t, 2 H, J = 7.7 Hz), 1.66 (d, 2 H, J = 11.2 Hz), 1.86 (t, 2 H, J = 10.8 Hz), 2.76 (d, 2 H, J = 11.1 Hz), 3.13 (t, 2 H, J = 7.6 Hz), 3.37 (s, 2 H), 3.73 (s, 3 H), 6.11 (s, 2 H), 6.79-6.81 (m, 1 H), 6.84-6.86 (m, 2 H), 6.88 (s, 1 H), 7.11 (s, 1 H), 7.21 (t, 1 H, J = 7.9 Hz); MS (ESI): m/z 435 [M + H] ⁺. |
| 40 | 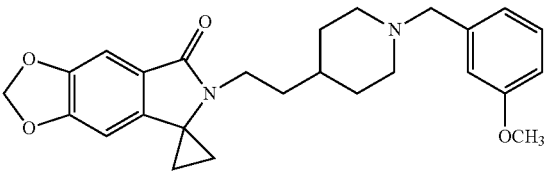<br>I-27 | ¹H NMR (DMSO-d₆): δ 1.12-1.20 (m, 3 H), 1.33 (t, 2 H, J = 6.4 Hz), 1.40 (q, 2 H, J = 6.4 Hz), 1.57 (t, 2 H, J = 7.7 Hz), 1.66 (d, 2 H, J = 11.0 Hz), 1.90 (t, 2 H, J = 10.4 Hz), 2.78 (d, 2 H, J = 11.3 Hz), 3.13 (t, 2 H, J = 7.7 Hz), 3.41 (s, 2 H), 3.76 (s, 3 H), 6.10 (s, 2 H), 6.88 (s, 1 H), 6.91 (d, 1 H, J = 7.4 Hz), 6.95 (s, 1 H), 7.11 (s, 1 H), 7.21 (t, 1 H, J = 7.3 Hz), 7.29 (d, 1 H, J = 7.4 Hz); MS (ESI): m/z 435 [M + H] ⁺. |
| 41 | 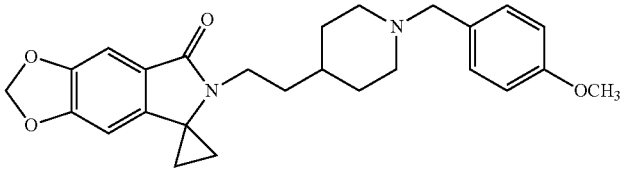<br>I-28 | ¹H NMR (DMSO-d₆): δ 1.13-1.16 (m, 2 H), 1.23 (br s, 1 H), 1.39 (t, 2 H, J = 6.9 Hz), 1.38 (q, 2 H, J = 6.6 Hz), 1.57 (t, 2 H, J = 7.5 Hz), 1.65 (d, 2 H, J = 11.4 Hz), 1.83 (t, 2 H, J = 11.0 Hz), 2.74 (d, 2 H, J = 11.1 Hz), 3.12 (t, 2 H, J = 7.6 Hz), 3.34 (s, 2 H) , 3.73 (s, 3 H), 6.10 (s, 2 H), 6.86 (d, 2 H, J = 8.5 Hz), 6.88 (s, 1 H), 7.10 (s, 1 H), 7.17 (d, 2 H, J = 8.4 Hz); MS (ESI): m/z 435 [M + H] ⁺. |

Example 42

Preparation of 6-[2-[1-(2-pyridylmethyl)-4-piperidyl]ethyl]spiro[[1,3]dioxolo[4,5-f]isoindole-7,1'-cyclopropane]-5-one (compound I-29)

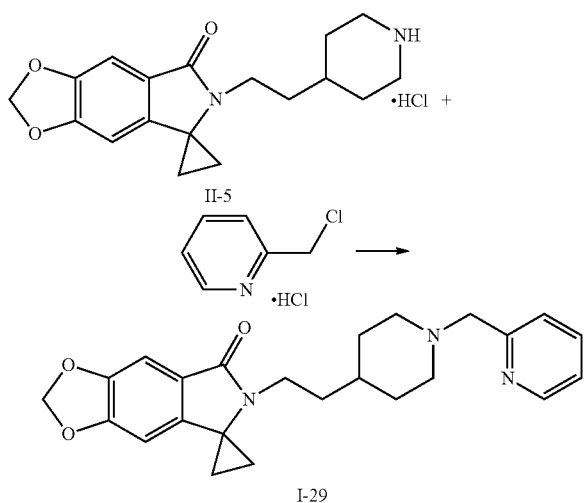

To a reaction vessel, 24.3 g (0.069 mol) compound II-5, 36.5 g (0.26 mol) potassium carbonate, 243 ml ethanol, 6.1 ml (0.044 mol) triethylamine were added. The mixture was heated to about 50° C., 31.5 g (0.049 mol) 2-chloromethylpyridine hydrochloride was added, the reaction was kept at 50° C. for 5 h, 750 ml water was added, solid was precipitated out, filtered, the filter cake was washed with water, dried, and 17.8 g compound I-29 was obtained, with yield of 63.4%. ¹H NMR (CDCl₃): δ 1.26 (dd, 2H, J=6.1, 7.6 Hz), 1.35 (br s, 3H), 1.49-1.57 (m, 4H), 1.72 (d, 2H, J=8.6 Hz), 2.08 (t, 2H, J=10.4 Hz), 2.89 (d, 2H, J=10.7 Hz), 3.19 (t, 2H, J=7.9 Hz), 3.64 (s, 2H), 6.03 (s, 2H), 6.42 (s, 1H), 7.15 (dd, 1H, J=5.2, 6.7 Hz), 7.24 (s, 1H), 7.41 (d, 1H, J=7.7 Hz), 7.64 (td, 1H, J=7.6, 1.8 Hz), 8.55 (d, 1H, J=4.2 Hz); MS (ESI): m/z 406 [M+H]⁺.

The following compounds were prepared according to the method in example 42, by using compound II-5 as the raw material and using appropriate reagents:

| Example | structure | $^1$H NMR (400 MHz) and MS (m/z) |
|---|---|---|
| 43 | I-30 | $^1$H NMR (CDCl$_3$): δ 1.25-1.36 (m, 5 H), 1.50-1.56 (m, 4 H), 1.73 (d, 2 H, J = 11.8 Hz), 1.99 (t, 2 H, J = 10.6 Hz), 2.84 (d, 2 H, J = 11.3 Hz), 3.19 (t, 2 H, J = 7.7 Hz), 3.49 (s, 2 H), 6.03 (s, 2 H), 6.43 (s, 1 H), 7.23-7.29 (m, 2 H), 7.67 (d, 1 H, J = 7.7 Hz), 8.50 (d, 1 H, J = 4.7 Hz), 8.52 (s, 1 H); MS (ESI): m/z 406 [M + H]$^+$. |
| 44 | I-31 | $^1$H NMR (CDCl$_3$): δ 1.25-1.34 (m, 5 H), 1.50-1.57 (m, 4 H), 1.73 (d, 2 H, J = 9.9 Hz), 1.99 (t, 2 H, J = 11.2 Hz), 2.82 (d, 2 H, J = 11.6 Hz), 3.19 (t, 2 H, J = 7.8 Hz), 3.47 (s, 2 H), 6.03 (s, 2 H), 6.43 (s, 1 H), 7.24 (s, 1 H), 7.26 (d, 2 H, J = 5.9 Hz), 8.53 (d, 2 H, J = 6.0 Hz); MS (ESI): m/z 406 [M + H]$^+$. |
| 45 | I-32 | $^1$H NMR (CDCl$_3$): δ 1.27 (t, 2 H, J = 6.4 Hz), 1.32-1.40 (m, 3 H), 1.43-1.57 (m, 4 H), 1.72 (d, 2 H, J = 10.0 Hz), 2.12 (t, 2 H, J = 10.9 Hz), 2.95 (d, 2 H, J = 11.4 Hz), 3.19 (t, 2 H, J = 7.9 Hz), 3.79 (s, 2 H), 6.03 (s, 2 H), 6.42 (s, 1 H), 7.19 (t, 1 H, J = 4.9 Hz), 7.24 (s, 1 H), 8.73 (d, 2 H, J = 4.9 Hz); MS (ESI): m/z 407 [M + H]$^+$. |

Example 46

Preparation of 6-[2-[1-(2-pyridylmethyl)-4-piperidyl]ethyl]spiro[[1,3]dioxolo[4,5-f]isoindole-7,1'-cyclopropane]-5-one hydrochloride (compound I-33)

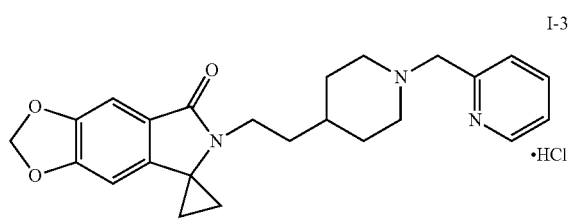

I-33

To a reaction vessel, 5 g (0.012 mol) compound I-29 and 25 ml ethanol were added, heated at 50° C. with stirring until dissolved completely, 1 ml (0.012 mol) concentrated hydrochloric acid was added, 1 g activated carbon was added and decolorized for 20 min, filtered, the filtrate was cooled to room temperature, 50 ml isopropyl ether was added dropwise, solid was precipitated out, stirred for 1 h, filtered, the filter cake was washed with a minor amount of isopropyl ether, dried, and 5 g compound I-33 was obtained, with yield of 91.7%. It can be further refined with ethanol/isopropyl ether, with yield of about 90%. $^1$H NMR (D$_2$O): δ 1.14 (t, 2H, J=7.0 Hz), 1.38-1.70 (m, 7H), 1.96 (d, 2H, J=13.3 Hz), 2.99-3.14 (m, 4H), 3.50 (d, 2H, J=11.0 Hz), 4.37 (s, 2H), 5.93 (s, 2H), 6.28 (s, 1H), 6.75 (s, 1H), 7.47 (dd, 1H, J=5.6, 7.5 Hz), 7.55 (d, 1H, J=7.8 Hz), 7.91 (td, 1H, J=7.8, 1.7 Hz), 8.58 (d, 1H, J=4.4 Hz); MS (ESI): m/z 406 [M-Cl]$^+$.

Example 47

Preparation of 6-[2-(1-benzyl-4-piperidyl)ethyl]spiro[[1,3]dioxolo[4,5-f]isoindole-7,1'-cyclopropane]-5-one hydrochloride (compound I-34)

I-34

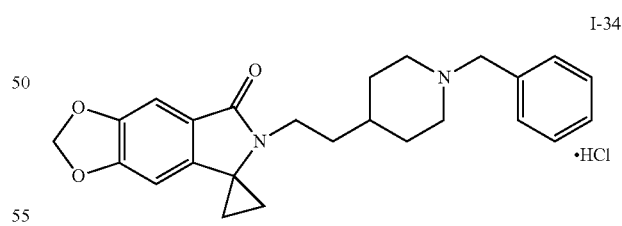

Compound I-34 was prepared according to the method in example 46, using 6-[2-(1-benzyl-4-piperidyl)ethyl]spiro[[1,3]dioxolo[4,5-f]isoindole-7,1'-cyclopropane]-5-one (compound I-17) as the raw material. $^1$H NMR (CDCl$_3$): $^1$H NMR (CDCl$_3$): δ 1.27 (dd, 2H, J=6.2, 7.5 Hz), 1.48-1.66 (m, 5H), 1.95-2.10 (m, 4H), 2.62 (ddd, 2H, J=4.6, 12.4, 22.2 Hz), 3.25 (t, 2H, J=6.7 Hz), 3.43 (d, 2H, J=11.3 Hz), 4.11 (d, 2H, J=5.0 Hz), 6.04 (s, 2H), 6.43 (s, 1H), 7.21 (s, 1H), 7.41-7.46 (m, 3H), 7.62 (dd, 2H, J=2.3, 5.9 Hz), 12.31 (br s, 1H); MS (ESI): m/z 405 [M-Cl]$^+$.

Example 48

Preparation of 6-[2-[1-(2-pyridylmethyl)-4-piperidyl]ethyl]spiro[[1,3]dioxolo[4,5-f]isoindole-7,1'-cyclopropane]-5-one phosphate (compound I-35)

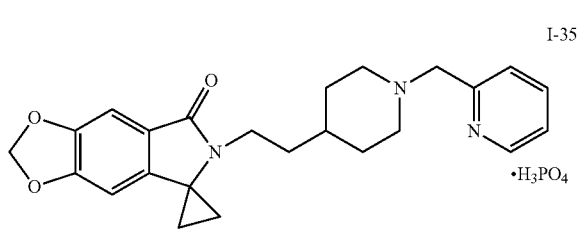

I-35

·H$_3$PO$_4$

To a reaction vessel, 2 g (0.0049 mol) compound I-29 and 40 ml ethanol were added, heated at 60° C. with stirring until dissolved completely, 0.57 g (0.0049 mol) 85% phosphoric acid was added, stirred, solid was precipitated out, 40 ml ethyl acetate was added dropwise, cooled to room temperature, stirred for 1 h, filtered, the filter cake was washed with a minor amount of ethyl acetate, dried, and 2.1 g compound I-35 was obtained, with yield of 84.7%. $^1$H NMR (D$_2$O): δ 1.10 (t, 2H, J=7.2 Hz), 1.33-1.64 (m, 7H), 1.92 (d, 2H, J=13.4 Hz), 2.95-3.09 (m, 4H), 3.46 (d, 2H, J=10.7 Hz), 4.34 (s, 2H), 5.89 (s, 2H), 6.20 (s, 1H), 6.69 (s, 1H), 7.45 (dd, 1H, J=5.2, 7.4 Hz), 7.53 (d, 1H, J=7.8 Hz), 7.88 (td, 1H, J=7.7, 1.2 Hz), 8.54 (d, 1H, J=4.6 Hz).

Example 49

Preparation of 6-[2-[1-(2-pyridylmethyl)-4-piperidyl]ethyl]-[1,3]dioxolo[4,5-f]isoindole-5,7-dione (compound I-36)

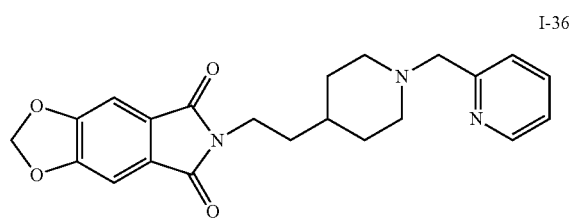 [SMILES: O=C1c2cc3c(cc2C(=O)N1CCC1CCN(Cc2ccccn2)CC1)OCO3]

I-36

Compound I-36 was prepared according to the method in example 3, using 6-[2-(4-piperidyl)ethyl]-[1,3]dioxolo[4,5-f]isoindole-5,7-dione hydrochloride (compound II-1) and 2-chloromethylpyridine hydrochloride as the raw materials: $^1$H NMR (DMSO-d$_6$): δ 1.12-1.19 (m, 3H), 1.48 (q, 2H, J=6.1 Hz), 1.67 (d, 2H, J=9.4 Hz), 1.94 (t, 2H, J=10.3 Hz), 2.76 (d, 2H, J=11.2 Hz), 3.54 (m, 4H), 6.27 (s, 2H), 7.24 (dd, 1H, J=6.8, 5.4 Hz), 7.38 (s, 2H), 7.42 (d, 1H, J=7.8 Hz), 7.74 (td, 1H, J=7.7, 1.4 Hz), 8.64 (d, 1H, J=4.2 Hz): m/z 394 [M+H]$^+$.

Example 50

Preparation of 6-[2-[1-(pyridazin-3-ylmethyl)-4-piperidyl]ethyl]-[1,3]dioxolo[4,5-f]isoindole-5,7-dione (compound I-37)

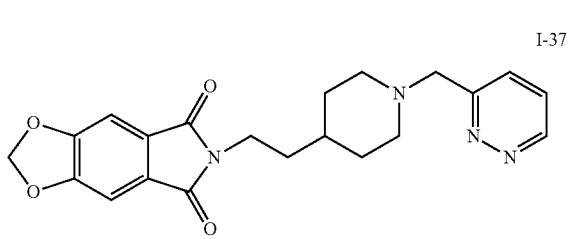 [SMILES: O=C1c2cc3c(cc2C(=O)N1CCC1CCN(Cc2cccnn2)CC1)OCO3]

I-37

Compound I-37 was prepared according to the method in example 3, using 6-[2-(4-piperidyl)ethyl]-[1,3]dioxolo[4,5-f]isoindole-5,7-dione hydrochloride (compound II-1) and 3-bromomethylpyridazine hydrobromide as the raw materials: $^1$H NMR (CDCl$_3$): δ 1.26-1.32 (m, 3H), 1.58 (q, 2H, J=5.0 Hz), 1.75 (d, 2H, J=8.9 Hz), 2.12 (t, 2H, J=10.6 Hz), 2.81 (d, 2H, J=11.1 Hz), 3.65 (t, 2H, J=7.2 Hz), 3.84 (s, 2H), 6.15 (s, 2H), 7.19 (s, 2H), 7.45 (dd, 1H, J=8.4, 4.9 Hz), 7.66 (dd, 1H, J=8.4, 1.2 Hz), 9.07 (dd, 1H, J=4.8, 1.6 Hz): m/z 395 [M+H]$^+$.

Example 51

Preparation of 6-[2-[1-(pyridazin-3-ylmethyl)-4-piperidyl]ethyl]spiro[[1,3]dioxolo[4,5-f]isoindole-7,1'-cyclopropane]-5-one (compound I-38)

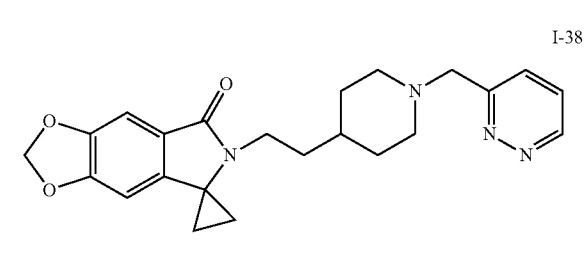 [SMILES: O=C1c2cc3c(cc2C2(CC2)N1CCC1CCN(Cc2cccnn2)CC1)OCO3]

I-38

Compound I-38 was prepared according to the method in example 42, using 6-[2-(4-piperidyl)ethyl]spiro[[1,3]dioxolo[4,5-f]isoindole-7,1'-cyclopropane]-5-one hydrochloride (compound II-5) and 3-bromomethylpyridazine hydrobromide as the raw materials: $^1$H NMR(CDCl$_3$): δ 1.25-1.37 (m, 5H), 1.49-1.58 (m, 4H), 1.73 (d, 2H, J=11.2 Hz), 2.14 (t, 2H, J=10.7 Hz), 2.82 (d, 2H, J=11.6 Hz), 3.19 (t, 2H, J=7.8 Hz), 3.85 (s, 2H), 6.03 (s, 2H), 6.43 (s, 1H), 7.23 (s, 1H), 7.46 (dd, 1H, J=8.4, 4.9 Hz), 7.67 (d, 1H, J=8.0 Hz), 9.08 (dd, 1H, J=4.8, 1.4 Hz): m/z 407 [M+H]$^+$.

Example 52

Preparation of 6-[2-[1-(1H-pyrrol-2-ylmethyl)-4-piperidyl]ethyl]spiro[[1,3]dioxolo[4,5-f]isoindole-7,1'-cyclopropane]-5-one (compound I-39)

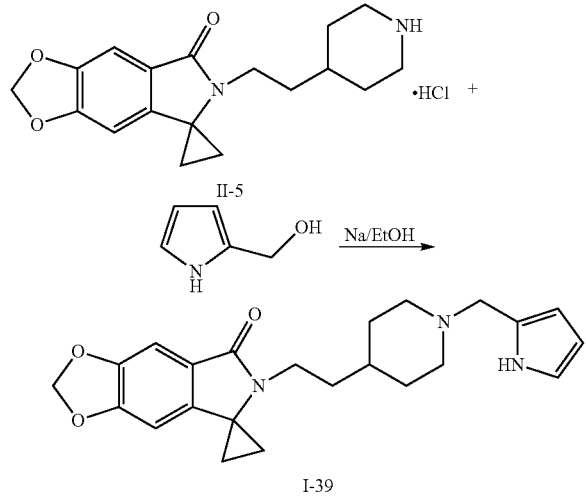

To a reaction vessel, 100 ml anhydrous ethanol and 1.4 g (0.061 mol) sodium were added. After the reaction was complete, 4.2 g (0.043 mol) 1H-pyrrol-2-ylmethanol and 2.5 g (0.0071 mol) compound 11-5 were added. The mixture was heated to reflux for 3 h until the reaction was complete, ethyl acetate and water were added, extracted, washed, the organic layer was collected, dried over anhydrous sodium sulfate, filtered, the filtrate was concentrated to dry, separated by column chromatography, and 1.5 g compound I-39 was obtained. $^1$H NMR (DMSO-d$_6$): δ 1.10-1.19 (m, 3H), 1.33-1.40 (m, 4H), 1.57 (t, 2H, J=6.6 Hz), 1.64 (d, 2H, J=11.7 Hz), 1.81 (t, 2H, J=11.1 Hz), 2.74 (d, 2H, J=10.9 Hz), 3.13 (t, 2H, J=7.6 Hz), 3.34 (s, 2H), 5.83 (s, 1H), 5.90 (s, 1H), 6.10 (s, 2H), 6.61 (s, 1H), 6.88 (s, 1H), 7.10 (s, 1H), 10.60 (s, 1H): m/z 394 [M+H]$^+$.

Note: 1H-pyrrol-2-ylmethanol can be prepared from 1H-pyrrole-2-carboxaldehyde via reduction by sodium borohydride.

Example 53

Preparation of 6-[2-[1-[(5-methyl-1H-pyrrol-2-yl)methyl]-4-piperidyl]ethyl]spiro[[1,3]dioxolo[4,5-f]isoindole-7,1'-cyclopropane]-5-one (compound I-40)

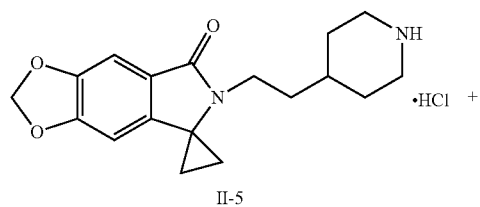

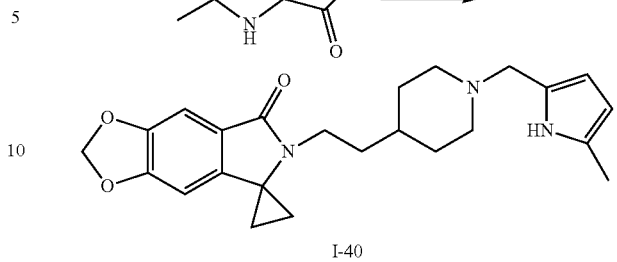

To a reaction vessel, 300 ml anhydrous ethanol, 10 g (0.029 mol) compound II-5, and 20 g (0.13 mol) ethyl 5-methyl-1H-pyrrole-2-carboxylate were added. The mixture was stirred at room temperature, 30 g (1.30 mol) sodium was added in batches, after the addition was complete, the mixture was heated to 60-70° C. and the reaction was kept for 5-6 h, after the reaction was complete, ethyl acetate and water were added, extracted, washed, the organic layer was collected, dried over anhydrous sodium sulfate, filtered, the filtrate was concentrated to dry, separated by column chromatography, and 2 g compound I-40 was obtained. $^1$H NMR (DMSO-d$_6$): δ 1.08-1.22 (m, 3H), 1.32-1.42 (m, 4H), 1.57 (t, 2H, J=7.0 Hz), 1.65 (d, 2H, J=11.5 Hz), 1.84 (t, 2H, J=9.1 Hz), 2.13 (s, 3H), 2.78 (d, 2H, J=10.2 Hz), 3.13 (t, 2H, J=7.5 Hz), 3.31 (s, 2H), 5.57 (s, 1H), 5.69 (s, 1H), 6.10 (s, 2H), 6.88 (s, 1H), 7.10 (s, 1H), 10.35 (s, 1H): m/z 408 [M+H]$^+$.

Example 54

Preparation of 6-[2-[1-(1H-pyrazol-5-ylmethyl)-4-piperidyl]ethyl]spiro[[1,3]dioxolo[4,5-f]isoindole-7,1'-cyclopropane]-5-one (compound I-41)

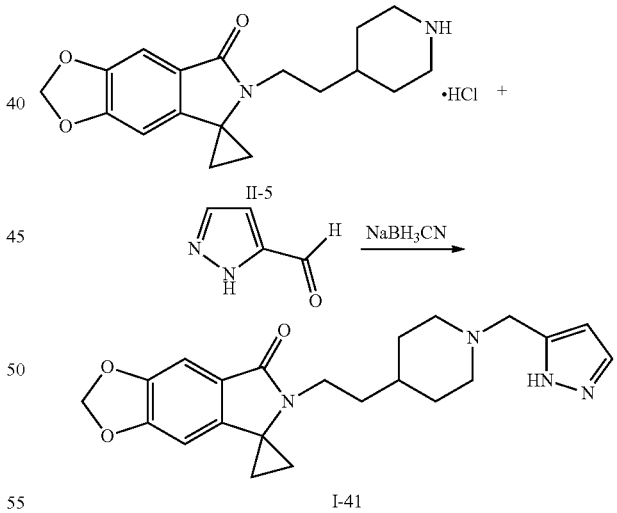

To a reaction vessel, 10 g (0.029 mol) compound II-5, 3.4 g (0.035 mol) 1H-pyrazole-5-carbaldehyde, and 150 ml anhydrous methanol were added while stirring, 3.6 ml (0.063 mol) acetic acid was added, stirred for 30 min, 2.5 g (0.040 mol) sodium cyanoborohydride was added, the reaction was kept at 50-60° C. for 6 h, cooled to room temperature, 150 ml water was added, the pH of the reaction mixture was adjusted to 8-9 with sodium hydroxide, and then 300 ml water was added dropwise, white solid was precipitated out, filtered, and 8.1 g compound I-41 was obtained. $^1$H NMR (DMSO-d$_6$): δ 1.09-1.21 (m, 3H), 1.33 (t, 2H, J=7.1 Hz), 1.40 (q, 2H, J=7.8 Hz), 1.57 (t, 2H, J=7.5 Hz), 1.65 (d, 2H, J=11.4 Hz), 1.89 (t, 2H, J=10.8 Hz), 2.77 (d, 2H, J=10.4 Hz), 3.12 (t, 2H, J=7.6 Hz), 3.45 (s, 2H), 6.10 (s, 3H), 6.88 (s, 1H), 7.11 (s, 1H), 7.56 (br s, 1H), 12.58 (br s, 1H): m/z 395 [M+H]$^+$.

Pharmacodynamic screening of the compounds according to the present invention was carried out according to the following procedures.

I. In Vitro Pharmacodynamic Screening

Modified Ellman method (Alvin V. et al. JWS-USC-75-IX Improves Information Processing and Cognitive Function in Animal Models[J]. Journal of Pharmacology and experimental therapeutics, 2010, 336(3): 751) was employed in the test, for testing the inhibition effect of a series of compounds of formula (I) on acetylcholinesterase, so that active AchEIs were screened out, and their activity were evaluated via the IC$_{50}$ value of inhibition of the series of compounds of formula (I) on the enzyme. The test results were shown in table 1:

TABLE 1

Data of inhibition activity of compound (I) on acetylcholinesterase

| Compound | IC$_{50}$ (nM) |
| --- | --- |
| DPH | 94 |
| I-1 | 86 |
| I-2 | 80 |
| I-3 | 269 |
| I-4 | 167 |
| I-5 | 502 |
| I-6 | 483 |
| I-7 | 486 |
| I-8 | 658 |
| I-9 | 601 |
| I-10 | 239 |
| I-11 | 889 |
| I-12 | >2000 |
| I-13 | >2000 |
| I-14 | >2000 |
| I-15 | >2000 |
| I-16 | >2000 |
| I-17 | 202 |
| I-18 | 154 |
| I-19 | 376 |
| I-20 | 706 |
| I-21 | 653 |
| I-22 | >2000 |
| I-23 | 959 |
| I-24 | >2000 |
| I-25 | 249 |
| I-26 | >2000 |
| I-27 | >2000 |
| I-28 | >2000 |
| I-29 | 903 |
| I-30 | >2000 |
| I-31 | >2000 |
| I-32 | >2000 |
| I-33 | 950 |
| I-34 | 197 |
| I-35 | 601 |
| I-36 | 161 |
| I-37 | 905 |
| I-38 | >2000 |
| I-39 | >2000 |
| I-40 | >2000 |
| I-41 | 990 |

Donepezil hydrochloride (DPH) was used in in vitro pharmacodynamic screening test as the positive control drug, and the results showed that compounds I-1 and I-2 have slightly higher potency than the positive control drug in enzymology levels; and I-3, I-4, I-10, I-17, I-18, I-25, I-34, and I-36 have slightly lower potency than the positive control drug; I-5, I-6, I-7, I-8, I-9, I-11, I-19, I-20, I-21, I-23, I-29, I-33, I-35, I-37, and I-41 are even lower; and I-12, I-13, I-14, I-15, I-16, I-22, I-24, I-26, I-27, I-28, I-30, I-31, I-32, I-38, I-39, and I-40 have relative low activity.

II. In Vivo Pharmacodynamic Screening

A. Improvement of a series of compounds of formula (I) on learning and memory disorder of mice induced by scopolamine.

Scopolamine is a competitive antagonist of central M cholinoceptor, and can block M1 receptor and M2 receptor, causing memory disorder, and becomes a model of senile dementia. Pharmacodynamic screening of a series of compounds of formula (I) was carried out, by using donepezil hydrochloride (DPH) as the positive control drug. Morris water maze test were performed on animals after administration for 3-5 days.

Test Materials:
1. Test Animals:
    Male C57 mice, 22±2 g. The animals were fed in light: dark cycle (10 h/14 h) in a cleaning level of animal room, ad lib. The tests were performed after 1 week acclimation;
2. Test Instrument:
    Morris water maze.
3. Test Drug:
    Scopolamine, donepezil hydrochloride (DPH), a series of compounds of formula (I).

Test Method:
1. Grouping of Animals and Dosage Regimen:
    The animals were randomly divided into groups (15 animals per group) by weight, including normal group, scopolamine group, donepezil hydrochloride (DPH) group, and groups of a series of compounds of formula (I). The animals were dosed intragastrically (10 ml/kg). The normal group and the model group were dosed equal volume of solvent.
2. Morris Water Maze Test:
    2.1 Test Method and Procedure:
    Morris water maze consists of a round pool and an automatic image capturing and processing system. The monitoring device was started upon the animal entered into water, the path of movement was recorded, and related parameters were analyzed and reported automatically after the experiment was complete.

The inner space of the round pool in the morris water maze was divided into 4 quadrants which are equal in size. A platform was put at the central of quadrant I, and the position of the platform remains unchanged throughout the behavior test. An appropriate amount of water was added 1 day before the experiment, such that the platform was 1 cm submerged underwater. Edible white colorant (2 g/L) was added before the experiment, such that the water in the pool becomes milk white (the water in the pool was refreshed everyday during the experiment). The training stage of the experiment was lasted for 5 d, twice everyday. During training, scopolamine (1 mg/kg) was injected intraperitoneally 30 min before the training. Mice were put into the pool, facing to the wall, at quadrant III, the time required for the mice to find the concealed platform and stand onto it after being put into water was recorded, as latent period, represented by second (S). The mice were forced to stand on the platform for 10 s, after finding the platform. If the mice did not find the platform 60 s after being put into water, the latent period was recorded as 60 s, and the mice were gently dragged onto the platform and forced to stand for 10 s.

2.2 Experiment Projects
1. Place Navigation Test:
    It was applied for the test of the ability of mice to acquaire the learning and memory of water maze. In the test, the period required for the mice to find the platform and climb onto it, as well as the roadmap, was recorded, i.e. the latent period was recorded.
2. Spatial Probe Test:
    It was applied for the test of the ability of mice to keep the memory of the spatial position of the platform, after the mice had learned how to find the platform. After the spatial probe test was complete, the platform was removed. Mice was put into water at the same position, and the period required for the mice to reach the original position of the platform for the first time, and the times of accrosing the original platform, were recorded.

2.3 Determination of the Biochemical Indicators of Brain Tissues:

After the behavior test was complete, the mice were sacrificed, brain tissues were collected (operated on an ice plate) and prepared into 10% of tissue homogenate with pre-cooled physiological saline, centrifuged (3000 rpm, 10 min), and the supernatant was subjected to malonaldehyde (MDA) assay following the kits.

Test Results:

(1) Therapeutical Effects of I-17, I-18 and I-19 on Senile Dementia mice model induced by scopolamine The test was divided into normal group, scopolamine (1 mg/kg) group, donepezil hydrochloride (DPH) (5 mg/kg) group, I-17 (5 mg/kg) group, I-18 (5 mg/kg) group, and I-19 (5 mg/kg) group. The test results of Morris water maze test were shown in Table 2:

the platform, while increasing the times of crossing platform of the animals. They can improve the learning and memory disorder of the animals induced by scopolamine.

(2) Therapeutical Effects of I-3 and I-18 on Senile Dementia Mice Model Induced by Scopolamine The test was divided into normal group, scopolamine (1 mg/kg) group, donepezil hydrochloride (DPH) (5 mg/kg) group, I-3 (10 mg/kg) group, I-3 (5 mg/kg) group, I-18 (10 mg/kg) group, and I-18 (5 mg/kg) group. The test results of Morris water maze test were shown in Table 3:

TABLE 2

Results of Morris water maze test of I-17, I-18 and I-19 ($\bar{x} \pm SD$) latent period(s)

| Group | n | day 1 | day 2 | day 3 | day 4 | day 5 | times of crossing platform |
|---|---|---|---|---|---|---|---|
| normal | 15 | 59.0 ± 3.7 | 57.0 ± 8.6 | 52.0 ± 12.1 | 44.5 ± 9.7 | 47.7 ± 16.9 | 1.8 ± 3.2 |
| model | 15 | 58.3 ± 6.7 | 60 ± 0 | 55.1 ± 13.6 | 59.6 ± 1.5 | 57.1 ± 7.8 | 0.5 ± 0.6 |
| DPH | 15 | 60 ± 0 | 60 ± 0 | 51.3 ± 15.6 | 60 ± 0 | 57.7 ± 6.6 | 1.3 ± 1.5* |
| I-17 | 15 | 56.8 ± 8.6 | 60 ± 0 | 48.7 ± 15.7 | 56.7 ± 8.1 | 47.2 ± 13.4* | 1.8 ± 2.5* |
| I-18 | 15 | 60 ± 0 | 60 ± 0 | 53.1 ± 10.4 | 56.9 ± 8.2 | 56.8 ± 8.6 | 0.5 ± 0.6 |
| I-19 | 15 | 60 ± 0 | 60 ± 0 | 55.2 ± 11.8 | 57.3 ± 10.4 | 53.9 ± 12.4 | 0.8 ± 1.4 |

*$P < 0.05$, in comparison with model group.

The results showed that, in comparison with model group, I-17 shorten the latent period of animals for climbing onto the platform significantly, while increasing the times of crossing platform of the animals. It can improve the learning and memory disorder of the animals induced by scopolamine, and is superior to the donepezil hydrochloride group. I-18 and I-19 can shorten the latent period of animals for climbing onto

TABLE 3

Results of Morris water maze test of I-3 and I-18 ($\bar{x} \pm SD$) latent period(s)

| Group | n | day 1 | day 2 | day 3 | day 4 | day 5 | times of crossing platform |
|---|---|---|---|---|---|---|---|
| normal | 15 | 55.3 ± 9.0 | 49.3 ± 12.4 | 35.1 ± 11.1 | 18.6 ± 14.6 | 22.7 ± 14.0 | 3.1 ± 1.8 |
| model | 14 | 59.9 ± 0.3 | 58.2 ± 6.8 | 59.4 ± 2.3 | 49.7 ± 13.3 | 48.0 ± 13.5 | 1.4 ± 1.2 |
| DPH | 15 | 57.1 ± 7.7 | 59.5 ± 2.1 | 58.2 ± 7.1 | 42.9 ± 19.2 | 45.5 ± 17.4 | 1.8 ± 1.1 |
| I-3 (10 mg/kg) | 15 | 59.3 ± 2.6 | 56.3 ± 9.7 | 55.5 ± 9.5 | 49.4 ± 15.7 | 45.0 ± 15.0 | 1.1 ± 1.1 |
| I-3 (5 mg/kg) | 13 | 56.5 ± 8.5 | 56.5 ± 8.6 | 60 ± 0 | 43.9 ± 15.4 | 34.0 ± 19.5* | 1.9 ± 1.5 |
| I-18 (10 mg/kg) | 14 | 56.0 ± 9.9 | 52.4 ± 12.4 | 60 ± 0 | 48.8 ± 15.4 | 49.2 ± 15.9 | 1.5 ± 1.2 |
| I-18 (5 mg/kg) | 15 | 55.0 ± 10.3 | 55.9 ± 9.0 | 60 ± 0 | 51.8 ± 15.6 | 35.6 ± 15.4 | 1.5 ± 1.7 |

*$P < 0.05$, in comparison with model group.

The results showed that, in Morris water maze test, the latent period of each group had the tendency of decreasing by time, wherein, in comparison with model group, that of I-3 group decreases significantly, and was closed to or superior to the donepezil hydrochloride group. Compound I-3 might has the potency of improving the learning and memory disorder of mice induced by scopolamine.

(3) Therapeutical Effects of I-14, I-15, I-23 and I-29 on Senile dementia mice model induced by scopolamine The test was divided into normal group, scopolamine (1 mg/kg) group, donepezil hydrochloride (DPH) (5 mg/kg) group, I-14 (5 mg/kg) group, I-15 (5 mg/kg) group, I-23 (5 mg/kg) group, and I-29 (5 mg/kg) group. The test results of Morris water maze test were shown in Table 4, and the results of biochemical tests were shown in Table 5:

The results showed that, in comparison with model group, in Morris water maze test, the latent period of each group for climbing onto the platform become short by time, and the times of crossing platform, especially for I-29 group were often much more than or closed to the donepezil hydrochloride group. Meanwhile, each group can reduce the content of MDA in brains of the animals. Among others, the compound I-29 has significant antioxidation effect, and might has an impact on improving the learning and memory disorder of mice induced by scopolamine.

(4) Therapeutical Effects of I-9 and I-17 on Senile Dementia Mice model induced by scopolamine The test was divided into normal group, scopolamine (1 mg/kg) group, donepezil hydrochloride (DPH) (5 mg/kg) group, I-9 (10 mg/kg) group, I-9 (5 mg/kg) group, I-17 (10 mg/kg) group, and I-17 (5 mg/kg) group. The test results of Morris water maze test were shown in Table 6:

TABLE 4

Results of Morris water maze test of I-14, I-15, I-23 and I-29 ($\bar{x} \pm SD$)

| Group | n | day 1 | day 2 | day 3 | day 4 | day 5 | latent period(s) times of crossing platform |
|---|---|---|---|---|---|---|---|
| normal | 15 | 57.5 ± 5.8 | 50.3 ± 18.0 | 47.4 ± 15.1 | 43.1 ± 16.9 | 36.0 ± 18.5 | 2.4 ± 2.6 |
| model | 15 | 59.7 ± 1.2 | 57.5 ± 6.9 | 56.8 ± 8.4 | 53.5 ± 12.2 | 55.6 ± 12.5 | 0.8 ± 0.9 |
| DPH | 15 | 60 ± 0 | 59.6 ± 1.4 | 57.0 ± 8.0 | 57.2 ± 7.5 | 53.7 ± 11.5 | 1.6 ± 1.7* |
| I-14 | 15 | 57.1 ± 7.6 | 60 ± 0 | 60 ± 0 | 54.2 ± 8.9 | 49.9 ± 14.7 | 1.3 ± 1.8 |
| I-15 | 15 | 60 ± 0 | 58.9 ± 4.4 | 56.5 ± 8.3 | 57.8 ± 5.3 | 51.1 ± 10.9 | 1.9 ± 1.5* |
| I-23 | 13 | 57.8 ± 5.4 | 57.7 ± 7.1 | 55.5 ± 8.8 | 43.9 ± 14.1* | 51.8 ± 10.9 | 1.5 ± 1.5* |
| I-29 | 15 | 59.3 ± 2.7 | 54.6 ± 12.5 | 48.0 ± 15.8* | 46.0 ± 16.3 | 40.4 ± 21.6* | 1.5 ± 1.4* |

In comparison with model group, *$P < 0.05$.

TABLE 5

The results of biochemical tests of compound I-14, I-15, I-23 and I-29

| Group | n | Dosage (mg/kg) | MDA(nmol/mgprot) |
|---|---|---|---|
| normal | 15 | — | 7.85 ± 2.3 |
| model | 15 | — | 10.12 ± 4.7 |
| DPH | 15 | 5 | 8.44 ± 3.09 |
| I-14 | 15 | 5 | 7.36 ± 1.3* |
| I-15 | 15 | 5 | 7.41 ± 2.1* |
| I-23 | 13 | 5 | 6.53 ± 2.3* |
| I-29 | 15 | 5 | 6.66 ± 1.75* |

*$P < 0.05$, in comparison with model group.

TABLE 6

Results of Morris water maze test of I-9 and I-17 ($\bar{x} \pm SD$)

| Group | n | day 1 | day 2 | day 3 | day 4 | day 5 | latent period(s) times of crossing platform |
|---|---|---|---|---|---|---|---|
| normal | 15 | 55.7 ± 6.2 | 45.0 ± 18.8 | 44.6 ± 15.0 | 35.9 ± 16.8 | 28.0 ± 16.6 | 2.60 ± 2.10 |
| model | 15 | 58.4 ± 5.5 | 59.7 ± 1.3 | 55.3 ± 8.3 | 52.8 ± 10.3 | 50.6 ± 16.0 | 1.33 ± 1.23 |
| DPH | 15 | 58.8 ± 4.8 | 60 ± 0 | 54.4 ± 8.4 | 47.0 ± 14.7 | 48.1 ± 14.4 | 1.40 ± 1.40 |
| I-9 (10 mg/kg) | 15 | 58.3 ± 6.5 | 56.6 ± 9.1 | 56.5 ± 6.3 | 51.1 ± 11.6 | 49.2 ± 16.9 | 1.80 ± 1.74 |

TABLE 6-continued

Results of Morris water maze test of I-9 and I-17 ($\bar{x} \pm SD$) latent period(s)

| Group | n | day 1 | day 2 | day 3 | day 4 | day 5 | times of crossing platform |
|---|---|---|---|---|---|---|---|
| I-9 (5 mg/kg) | 15 | 58.9 ± 4.0 | 60 ± 0 | 51.2 ± 11.0 | 53.4 ± 11.8 | 51.1 ± 11.5 | 1.27 ± 1.44 |
| I-17 (10 mg/kg) | 15 | 59.9 ± 0.3 | 58.1 ± 6.2 | 51.1 ± 12.0 | 42.1 ± 15.5* | 39.3 ± 16.7* | 2.60 ± 1.96 |
| I-17 (5 mg/kg) | 15 | 57.3 ± 6.7 | 56.3 ± 9.1 | 52.5 ± 10.4 | 46.4 ± 16.6 | 43.7 ± 11.8 | 2.00 ± 1.41 |

*P < 0.05, in comparison with model group.

The results showed that, in comparison with model group, in Morris water maze place navigation test, the latent period of each group for climbing onto the platform had the tendency of decreasing by time. Wherein, that of I-17 group (10 mg/kg) was superior to donepezil hydrochloride group, and had a significant effect. In Morris water maze spatial probe test, the times of crossing platform of I-9 (10 mg/kg) group, I-17 (10 mg/kg) group, and I-17 (5 mg/kg) group were more than donepezil hydrochloride group. In Morris water maze test, the latent period of animals for climbing onto the platform and the times of crossing platform of I-17 (10 mg/kg) group were superior to donepezil hydrochloride group. Compound I-17 had the effect of improving the learning and memory disorder of mice induced by scopolamine B. Improvement of the Hydrochloride (I-33) of Compound I-29 on Learning and Memory Disorder of Mice Induced by Intracerebroventricular Injection of AρI-42.

The model of learning and memory disorder induced after intracerebroventricular injection of Aβ1-42 is the most common animal model for evaluating whether a compound has the effect of improving the learning and memory. This animal model break significantly the learning ability and memory function of an animal, and its mechanism of influencing the memory is known, the result is repeatable, and has no distinct non-specific effect. Morris water maze test and the model of learning and memory disorder induced by intracerebroventricular injection of Aβ1-42 were employed in the present research, and the improvement effects of I-33 on learning and memory of rats at various concentration (0.7 mg/Kg, 3.5 mg/Kg, and 7 mg/Kg) were evaluated.

Test Materials and Grouping:

1. Test Animals:

SD, male (220±20 g), the animals were fed in light: dark cycle (12 h/12 h) in a cleaning level of animal room, ad lib. The tests were performed after 3 days acclimation in the animal room. Aβ1-42 was formulated to 2 μg/μl according to the instruction of specification.

2. Grouping (1) Normal group: intracerebroventricular injection of physiological saline (2) Model group with intracerebroventricular injection of Aβ1-42: intracerebroventricular injection of Aβ1-42

(3) Donepezil hydrochloride control group: donepezil hydrochloride (DPH) (3 mg/Kg)+intracerebroventricular injection of Aβ1-42

(4) I-33 (low concentration group): I-33 (0.7 mg/Kg)+intracerebroventricular injection of Aβ1-42

(5) I-33 (medium concentration group): I-33 (3.5 mg/Kg)+intracerebroventricular injection of Aβ1-42

(6) I-33 (high concentration group): I-33 (7 mg/Kg)+intracerebroventricular injection of Aβ1-42

3. Test Instrument: Rat Morris water maze instrument, and brain stereotaxic apparatus.

4. Test reagents: Aβ1-42, donepezil hydrochloride (DPH), and I-33. Test method:

SD rats were randomly divided into normal control group, model group with intracerebroventricular injection of Aβ1-42, positive control group (donepezil hydrochloride, 3 mg/Kg), and the test drug I-33 groups (0.7 mg/kg, 3.5 mg/Kg and 7 mg/kg groups). Each rat in normal control group received intracerebroventricular injection of 5 μl of physiological saline, each rat in the other groups received intracerebroventricular injection of 5 μl of Aβ1-42. After the operation, the rats received the following tests after 1 week recovery period. Correspond solvent was administered to the rats in normal control group and the model group with intracerebroventricular injection of Aβ1-42 at a fixed time in the morning everyday, by intragastric administration; and the rats in I-33 groups and donepezil hydrochloride control group were administered with corresponding amount of the drugs, depending on the body weight. The drugs were administered for 8 days, the training for water maze test was started on the 5th day, and the water maze test was formally started on the 9th day.

Test results: as shown in Table 7.

(1) There is no significant statistic difference of the swimming speed of the rat in each group, indicating that the rats have the same status.

(2) After intracerebroventricular injection of Aβ1-42 (10 μg/rat) to rats, the period required for reaching the platform for the first time (latent period) was significantly prolonged. donepezil hydrochloride (DPH) (3 mg/Kg) can fight against the effect of Aβ1-42, and significantly shorten the period required for reaching the platform for the first time. All of the various dosage of I-33 being tested can significantly shorten the period required for reaching the platform for the first time (latent period).

(3) After intracerebroventricular injection of Aβ1-42 (10 μg/rat) to rats, the times of crossing the platform were significantly decreased. Donepezil hydrochloride (DPH) (3 mg/Kg) can fight against the effect of Aβ1-42, and significantly increases the times of crossing the platform. All of the various dosage of I-33 being tested can significantly increases the times of crossing the platform.

TABLE 7

Improvement of I-33 on learning and memory disorder induced by intracerebroventricular injection of 41-42 ($\bar{x} \pm$ SD)

| Group | Swimming speed | The period of reaching the platform for the first time (latent period) | Times of crossing platform |
|---|---|---|---|
| normal | 32.95 ± 1.56 | 20.03 ± 4.16* | 3.23 ± 0.50* |
| Aβ group | 31.25 ± 2.00 | 50.10 ± 7.96 | 1.58 ± 0.36 |
| DPH + Aβ group | 30.07 ± 2.48 | 23.94 ± 4.84* | 3.22 ± 0.55* |
| I-33 low concentration + Aβ group | 27.27 ± 3.63 | 21.37 ± 3.64* | 3.00 ± 0.33* |
| I-33 medium concentration + Aβ group | 32.13 ± 2.06 | 18.10 ± 6.54* | 3.40 ± 0.43* |
| I-33 high concentration + Aβ group | 34.07 ± 2.93 | 14.87 ± 3.62* | 3.20 ± 0.36* |

*$P < 0.05$, in comparison with Aβ group.

The results showed that, in Morris water maze, all of the various dosage of I-33 being tested can significantly improve the learning and memory disorder of rats induced by intracerebroventricular injection of Aβ1-42, and is dosage-dependent.

Acute Toxicity Test

Preliminary acute toxicity test was performed on white mice, for testing the hydrochloride (I-33) of a representative compound according to the present invention, i.e. compound I-29, and the hydrochloride (I-34) of a representative compound according to the present invention, i.e. compound I-17, with reference to the Guiding Principles on Acute Toxicity Test Technique of Chemical Drugs.

Test Methods:

Firstly, preliminary tests were performed, in order to determine the concentration of each compound, with just 0% mortality or just 100% mortality, before starting the formal tests. The animals were divided into groups by weight, various dosages of drugs were administered between 0%-100%. Dosage volume: 10 ml/kg. Dosage manner: intravenous injection or intragastric administration.

A. Acute Toxicity Test of Donepezil Hydrochloride

1. Intravenous Injection:

The animals were divided into 6 groups, with 5 animals per group. The dosages for the 6 groups were 4.00 mg/kg, 3.60 mg/kg, 3.24 mg/kg, 2.92 mg/kg, 2.62 mg/kg and 2.36 mg/kg, respectively. Each animal was injected once at tail vein, and was observed for 1 W.

2. Intragastric Administration:

The animals were divided into 6 groups, with 5 animals per group. The dosages for the 6 groups were 64.80 mg/kg, 58.32 mg/kg, 42.51 mg/kg, 38.27 mg/kg, 34.44 mg/kg and 30.99 mg/kg, respectively. Each animal was fasted 12 h before administration. Each animal received intragastric administration once, and was observed for 1 W.

B. Acute Toxicity Test of I-33

1. Intravenous Injection:

The animals were divided into 6 groups, with 5 animals per group. The dosages for the 6 groups were 50.00 mg/kg, 40.00 mg/kg, 32.00 mg/kg, 25.60 mg/kg, 20.48 mg/kg and 16.18 mg/kg, respectively. Each animal was injected once at tail vein, and was observed for 1 W.

2. Intragastric Administration:

The animals were divided into 6 groups, with 5 animals per group. The dosages for the 6 groups were 500.00 mg/kg, 450.00 mg/kg, 295.25 mg/kg, 265.72 mg/kg, 239.15 mg/kg and 215.23 mg/kg, respectively. Each animal was fasted 12 h before administration. Each animal received intragastric administration once, and was observed for 1 W.

C. Acute Toxicity Test of I-34

1. Intravenous Injection:

The animals were divided into 5 groups, with 5 animals per group. The dosages for the 5 groups were 25.60 mg/kg, 23.04 mg/kg, 20.25 mg/kg, 18.23 mg/kg and 16.40 mg/kg, respectively. Each animal was injected once at tail vein, and was observed for 1 W.

2. Intragastric Administration:

The animals were divided into 5 groups, with 5 animals per group. The dosages for the 5 groups were 300.00 mg/kg, 240.00 mg/kg, 192.00 mg/kg, 153.60 mg/kg and 122.88 mg/kg, respectively. Each animal was fasted 12 h before administration. Each animal received intragastric administration once, and was observed for 1 W.

Observed Indicators:

The toxic reaction and death of the animals after administration were observed, and mortality was counted. The results were analyzed with LD50 data processing software.

Test results: as shown in Table 8.

TABLE 8

Test results of acute toxicity tests of I-33 and I-34

| Compound | Route of administration | dosage (mg/kg) | Number of animals | Number of death | Mortality (%) | Median lethal dose LD50 (mg/kg) | 95% Confidence LD50 (mg/kg) |
|---|---|---|---|---|---|---|---|
| donepezil hydrochloride | Intravenous injection | 4.00 | 5 | 5 | 100 | 3.07 | 3.02 ≤ LD50 ≤ 3.13 |
| | | 3.60 | 5 | 4 | 60 | | |
| | | 3.24 | 5 | 3 | 60 | | |
| | | 2.92 | 5 | 2 | 40 | | |
| | | 2.62 | 5 | 1 | 20 | | |
| | | 2.36 | 5 | 0 | 0 | | |
| | Intragastric administration | 64.80 | 5 | 5 | 100 | 42.52 | 30.13 ≤ LD50 ≤ 60.00 |
| | | 58.32 | 5 | 4 | 80 | | |
| | | 42.51 | 5 | 3 | 60 | | |
| | | 38.27 | 5 | 2 | 40 | | |
| | | 34.44 | 5 | 1 | 40 | | |
| | | 30.99 | 5 | 0 | 0 | | |

TABLE 8-continued

Test results of acute toxicity tests of I-33 and I-34

| Compound | Route of administration | dosage (mg/kg) | Number of animals | Number of death | Mortality (%) | Median lethal dose LD50 (mg/kg) | 95% Confidence LD50 (mg/kg) |
|---|---|---|---|---|---|---|---|
| I-33 | Intravenous injection | 50.00 | 5 | 5 | 100 | 31.30 | 8.77 ≤ LD50 ≤ 111.69 |
|  |  | 40.00 | 5 | 4 | 80 |  |  |
|  |  | 32.00 | 5 | 3 | 60 |  |  |
|  |  | 25.60 | 5 | 1 | 20 |  |  |
|  |  | 20.48 | 5 | 0 | 0 |  |  |
|  |  | 16.18 | 5 | 0 | 0 |  |  |
|  | Intragastric administration | 500.00 | 5 | 5 | 100 | 303.13 | 176.25 ≤ LD50 ≤ 521.34 |
|  |  | 450.00 | 5 | 4 | 80 |  |  |
|  |  | 295.25 | 5 | 3 | 60 |  |  |
|  |  | 265.72 | 5 | 2 | 40 |  |  |
|  |  | 239.15 | 5 | 1 | 0 |  |  |
|  |  | 215.23 | 5 | 0 | 0 |  |  |
| I-34 | Intravenous injection | 25.60 | 5 | 5 | 100 | 20.14 | 8.06 ≤ LD50 ≤ 50.51 |
|  |  | 23.04 | 5 | 4 | 80 |  |  |
|  |  | 20.25 | 5 | 3 | 60 |  |  |
|  |  | 18.23 | 5 | 1 | 20 |  |  |
|  |  | 16.40 | 5 | 0 | 0 |  |  |
|  | Intragastric administration | 300.00 | 5 | 5 | 100 | 171.20 | 96.23 ≤ LD50 ≤ 304.59 |
|  |  | 240.00 | 5 | 4 | 80 |  |  |
|  |  | 192.00 | 5 | 3 | 60 |  |  |
|  |  | 153.60 | 5 | 2 | 40 |  |  |
|  |  | 122.88 | 5 | 0 | 0 |  |  |

The results of preliminary tests showed that, the median lethal dose of I-33 by oral administration and intravenous administration were 8-10 times of those of donepezil hydrochloride, respectively; and the median lethal dose of I-34 by oral administration and intravenous administration were 4-7 times of those of donepezil hydrochloride, respectively. Both I-33 and I-34 exhibited lower toxicity than donepezil hydrochloride, had better safety.

Researches on Pharmacokinetics

Researches on oral plasma pharmacokinetics of the hydrochloride (I-33) of a representative compound according to the present invention, i.e. compound I-29, and phosphate thereof (I-35) were performed on rat, with reference to the Guiding Principles on Preclinical Researches on Pharmacokinetics.

Test Methods and Results:

Various drugs were orally administered to rats, including donepezil hydrochloride-dosed group, I-35-dosed group, and I-33-dosed group, respectively, the dosage were 5 mg/kg and the dosage volume were 10 mL/kg. Venous blood was collected from postocular venous plexus of rats, 0.083, 0.167, 0.333, 0.666, 1.0, 2.0, 3.0, 4.0, 6.0, 8.0, 12, 24, 36, 48, 72 and 96 h after administration, 6 rats were used at each time point. 0.3 ml of whole blood was collected at corresponding time point, anticoagulating with heparin, centrifuged at 4000 rpm for 10 min, the plasma was separated, 50 μL the plasma sample of rats was collected, 100 μL acetonitrile (containing 0.1% formic acid) was added, mixed under vortex for 1 min, centrifuged (12000 rpm) for 10 min, the supernatant was collected, analyzed with liquid chromatography-mass spectrometer, the area of peaks were recorded and used for the calculation of blood drug concentration, and the drug-time curve was plotted. Meanwhile, it was fitted automatically with DAS 2.0 pharmacokinetics software from Chinese Pharmacological Society, the corresponding pharmacokinetics parameters were shown in Table 9 and FIG. 1:

TABLE 9

Test results of rat plasma pharmacokinetics after oral administration of I-33 and I-35

| Parameters | donepezil hydrochloride (5 mg/kg) | I-33(5 mg/kg) | I-35(5 mg/kg) |
|---|---|---|---|
| AUC(0-t) | 1370.709 ± 311.367 | 4933.099 ± 1397.72 | 5165.211 ± 441.415 |
| AUC(0-∞) | 1415.126 ± 337.151 | 4990.306 ± 1423.91 | 5222.684 ± 433.165 |
| MRT(0-t) | 2.734 ± 0.251 | 2.212 ± 0.389 | 2.343 ± 0.206 |
| MRT(0-∞) | 3.119 ± 0.404 | 2.352 ± 0.373 | 2.483 ± 0.265 |
| t1/2z | 2.473 ± 0.449 | 2.085 ± 0.392 | 1.965 ± 0.296 |
| Tmax | 0.389 ± 0.136 | 0.305 ± 0.068 | 0.555 ± 0.172 |
| Cmax | 638.5 ± 127.792 | 2463.333 ± 385.73 | 2111.667 ± 331.748 |

The results showed that, at the same dosage, in comparison with donepezil hydrochloride, the absorption degree (AUC) and peak concentration (Cmax) of I-33 and I-35 were significantly higher than those of donepezil hydrochloride.

In conclusion, among the compounds provided in the present invention, I-1, I-2, I-4 and I-17 or hydrochloride (I-34) thereof have comparable inhibition activity on acetylcholinesterase with donepezil hydrochloride. In comparison to donepezil hydrochloride, in Morris water maze, I-17 and I-29 or hydrochloride (I-33) thereof exhibited stronger effects of improving learning and memory, and exhibited better efficiency in vivo. I-29 or hydrochloride (I-33) thereof are of particular attention, although the inhibition activity of this compound on acetylcholinesterase is relatively weak in vitro, i.e. about 10% of donepezil hydrochloride, it has much higher in vivo efficiency than donepezil hydrochloride, and has stronger antioxidation effect in comparison to donepezil hydrochloride, indicating that the effect of improving learning and memory of I-29 might induced by other routes, in addition to its effect on acetylcholinesterase. Another exciting test result is: in preliminary acute toxicity tests on white rats, the hydrochloride (I-33) of I-29 exhibited much lower toxicity, even down to one tenth of the toxicity of donepezil hydrochloride, and thus this compound has great potential, and the pains caused by the toxic and adverse effects caused by current drugs can be reduced significantly, showing the promising prospect of compound I-29.

All of the references mentioned in the present invention are cited by reference, as each reference is cited by reference separately. It should be appreciated that, after reading the above contents of the present invention, a person skilled in the art can make various changes or modifications to the present invention, and such equivalents also falls within the scope of the present invention, as defined in accompanying claims.

The invention claimed is:

1. A compound represented by formula (I)

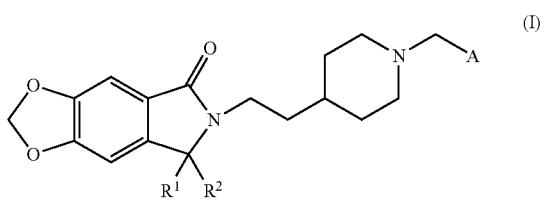

(I)

or a pharmaceutically acceptable salt, wherein:
$R^1$ and $R^2$ together is =O; or, $R^1$ and $R^2$ together with the carbon atom connecting them can form a 3-membered carbon ring;
A is selected from the group consisting of phenyl, $R^3$-substituted phenyl, pyridinyl, $R^4$-substituted pyridinyl, pyrimidinyl, $R^5$-substituted pyrimidinyl, pyrrolyl, $R^6$-substituted pyrrolyl, pyridazinyl, $R^7$-substituted pyridazinyl, pyrazolyl, and $R^8$-substituted pyrazolyl;
$R^3$ is 1 to 5 substituents independently selected from the group consisting of halogen, $(C_1-C_3)$ alkyl, $(C_2-C_3)$ alkenyl, $(C_3-C_4)$ cycloalkyl, $(C_1-C_3)$ alkoxy, trifluoromethyl and cyano;
$R^4$ is 1 to 4 substituents independently selected from the group consisting of halogen, $(C_1-C_3)$ alkyl, $(C_2-C_3)$ alkenyl, $(C_3-C_4)$ cycloalkyl, $(C_1-C_3)$ alkoxy, trifluoromethyl and cyano;
$R^5$ is 1 to 3 substituents independently selected from the group consisting of halogen, $(C_1-C_3)$ alkyl, $(C_2-C_3)$ alkenyl, $(C_3-C_4)$ cycloalkyl, $(C_1-C_3)$ alkoxy, trifluoromethyl and cyano;
$R^6$ is 1 to 4 substituents independently selected from the group consisting of $(C_1-C_3)$ alkyl, $(C_2-C_3)$ alkenyl and $(C_3-C_4)$ cycloalkyl;
$R^7$ is 1 to 3 substituents independently selected from the group consisting of halogen, $(C_1-C_3)$ alkyl, $(C_2-C_3)$ alkenyl, $(C_3-C_4)$ cycloalkyl, $(C_1-C_3)$ alkoxy, trifluoromethyl and cyano;
$R^8$ is 1 to 3 substituents independently selected from the group consisting of $(C_1-C_3)$ alkyl, $(C_2-C_3)$ alkenyl and $(C_3-C_4)$ cycloalkyl.

2. The compound according to claim 1, wherein A is selected from phenyl, $R^3$-substituted phenyl, pyridinyl, $R^4$-substituted pyridinyl, pyrimidinyl, $R^5$-substituted pyrimidinyl, pyrrolyl, $R^6$-substituted pyrrolyl, pyridazinyl, $R^7$-substituted pyridazinyl, pyrazolyl, or $R^8$-substituted pyrazolyl.

3. The compound according to claim 1, wherein $R^1$ and $R^2$ together with the carbon atom connecting them form a 3-membered carbon ring.

4. The compound according to claim 1, wherein A is selected from phenyl, $R^3$-substituted phenyl, pyridinyl, $R^4$-substituted pyridinyl, pyrimidinyl, $R^5$-substituted pyrimidinyl, pyrrolyl, $R^6$-substituted pyrrolyl, pyridazinyl, $R^7$-substituted pyridazinyl, pyrazolyl, or $R^8$-substituted pyrazolyl; wherein $R^3$ is 1 to 5 substituents independently selected from the group consisting of halogen, $(C_1-C_3)$ alkyl, $(C_1-C_3)$ alkoxy, trifluoromethyl and cyano; $R^4$ is 1 to 4 substituents independently selected from the group consisting of halogen, $(C_1-C_3)$ alkyl, $(C_1-C_3)$ alkoxy, trifluoromethyl and cyano; $R^5$ is 1 to 3 substituents independently selected from the group consisting of halogen, $(C_1-C_3)$ alkyl, $(C_1-C_3)$ alkoxy, trifluoromethyl and cyano; $R^6$ is 1 to 4 substituents independently selected from $(C_1-C_3)$ alkyl; $R^7$ is 1 to 3 substituents independently selected from the group consisting of halogen, $(C_1-C_3)$ alkyl, $(C_1-C_3)$ alkoxy, trifluoromethyl and cyano; and $R^8$ is 1 to 3 substituents independently selected from $(C_1-C_3)$ alkyl.

5. The compound according to claim 4, wherein A is selected from phenyl, $R^3$-substituted phenyl, pyridinyl, pyrimidinyl, pyrrolyl, $R^6$-substituted pyrrolyl, pyridazinyl, or pyrazolyl; wherein $R^3$ is 1 to 5 substituents independently selected from the group consisting of halogen, $(C_1-C_3)$ alkyl, $(C_1-C_3)$ alkoxy, trifluoromethyl and cyano; and $R^6$ is 1 to 4 substituents independently selected from $(C_1-C_3)$ alkyl.

6. The compound according to claim 5, wherein A is phenyl.

7. The compound according to claim 5, wherein A is selected from $R^3$-substituted phenyl, 2 fluorophenyl, 3-fluorophenyl, 4-fluorophenyl, or 2,6-difluorophenyl.

8. The compound according to claim 5, wherein A is selected from pyridinyl, 2 pyridinyl or 3-pyridinyl.

9. The compound according to claim 5, wherein A is selected from pyrimidinyl, or pyrimidin-2-yl.

10. The compound according to claim 5, wherein A is selected from pyrrolyl, or pyrrol-2-yl.

11. The compound according to claim 5, wherein A is selected from $R^6$-substituted pyrrolyl, 5 methylpyrrol-2-yl.

12. The compound according to claim 5, wherein A is selected from pyridazinyl, pyridazin-3-yl.

13. The compound according to claim 5, wherein A is selected from pyrazolyl, 1H-pyrazol-5-yl.

14. The compound according to claim 1, wherein said compound of formula (I) is selected from:
6-[2-(1-benzyl-4-piperidyl)ethyl]-[1,3]dioxolo[4,5-f] isoindole-5,7-dione (I–1);
6-[2-[1-[(2-fluorophenyl)methyl]-4-piperidyl]ethyl]-[1,3] dioxolo[4,5-f]isoindole-5,7-dione (I-2);
6-[2-[1-[(3-fluorophenyl)methyl]-4-piperidyl]ethyl]-[1,3] dioxolo[4,5-f]isoindole-5,7-dione (I-3);
6-[2-[1-[(4-fluorophenyl)methyl]-4-piperidyl]ethyl]-[1,3] dioxolo[4,5-f]isoindole-5,7-dione (I-4);
6-[2-(1-benzyl-4-piperidyl)ethyl]spiro[[1,3]dioxolo[4,5-f]isoindole-7,1'-cyclopropane]-5-one (I-17);
6-[2-[1-[(2-fluorophenyl)methyl]-4-piperidyl]ethyl]spiro [[1,3]dioxolo[4,5-f]isoindole-7,1'-cyclopropane]-5-one (I-18);
6-[2-[1-[(3-fluorophenyl)methyl]-4-piperidyl]ethyl]spiro [[1,3]dioxolo[4,5-f]isoindole-7,1'-cyclopropane]-5-one (I-19);
6-[2-[1-[(4-fluorophenyl)methyl]-4-piperidyl]ethyl]spiro [[1,3]dioxolo[4,5-f]isoindole-7,1'-cyclopropane]-5-one (I-20);
6-[2-[1-[(2-chlorophenyl)methyl]-4-piperidyl]ethyl]spiro [[1,3]dioxolo[4,5-f]isoindole-7,1'-cyclopropane]-5-one (I-21);
6-[2-[1-[[2-(trifluoromethyl)phenyl]methyl]-4-piperidyl] ethyl]spiro[[1,3]dioxolo[4,5-f]isoindole-7,1'-cyclopropane]-5-one (I-22);
6-[2-[1-(o-tolylmethyl)-4-piperidyl]ethyl]spiro[[1,3]dioxolo[4,5-f]isoindole-7,1'-cyclopropane]-5-one (I-23);
6-[2-[1-[(2-cyanophenyl)methyl]-4-piperidyl]ethyl]spiro [[1,3]dioxolo[4,5-f]isoindole-7,1'-cyclopropane]-5-one (I-24);
6-[2-[1-[(2,6-difluorophenyl)methyl]-4-piperidyl]ethyl] spiro[[1,3]dioxolo[4,5-f]isoindole-7,1'-cyclopropane]-5-one (I-25);

6-[2-[1-[(2-methoxyphenyl)methyl]-4-piperidyl]ethyl]spiro[[1,3]dioxolo[4,5-f]isoindole-7,1'-cyclopropane]-5-one (I-26);

6-[2-[1-[(3-methoxyphenyl)methyl]-4-piperidyl]ethyl]spiro[[1,3]dioxolo[4,5-f]isoindole-7,1'-cyclopropane]-5-one (I-27);

6-[2-[1-[(4-methoxyphenyl)methyl]-4-piperidyl]ethyl]spiro[[1,3]dioxolo[4,5-f]isoindole-7,1'-cyclopropane]-5-one (I-28);

6-[2-[1-(2-pyridylmethyl)-4-piperidyl]ethyl]spiro[[1,3]dioxolo[4,5-f]isoindole-7,1'-cyclopropane]-5-one (I-29);

6-[2-[1-(3-pyridylmethyl)-4-piperidyl]ethyl]spiro[[1,3]dioxolo[4,5-f]isoindole-7,1'-cyclopropane]-5-one (I-30);

6-[2-[1-(4-pyridylmethyl)-4-piperidyl]ethyl]spiro[[1,3]dioxolo[4,5-f]isoindole-7,1'-cyclopropane]-5-one (I-31);

6-[2-[1-(pyrimidin-2-ylmethyl)-4-piperidyl]ethyl]spiro[[1,3]dioxolo[4,5-f]isoindole-7,1'-cyclopropane]-5-one (I-32);

6-[2-[1-(2-pyridylmethyl)-4-piperidyl]ethyl]spiro[[1,3]dioxolo[4,5-f]isoindole-7,1'-cyclopropane]-5-one hydrochloride (I-33);

6-[2-(1-benzyl-4-piperidyl)ethyl]spiro[[1,3]dioxolo[4,5-f]isoindole-7,1'-cyclopropane]-5-one hydrochloride (I-34);

6-[2-[1-(2-pyridylmethyl)-4-piperidyl]ethyl]spiro[[1,3]dioxolo[4,5-f]isoindole-7,1'-cyclopropane]-5-one phosphate (I-35);

6-[2-[1-(2-pyridylmethyl)-4-piperidyl]ethyl]-[1,3]dioxolo[4,5-f]isoindole-5,7-dione (I-36);

6-[2-[1-(pyridazin-3-ylmethyl)-4-piperidyl]ethyl]-[1,3]dioxolo[4,5-f]isoindole-5,7-dione (I-37);

6-[2-[1-(pyridazin-3-ylmethyl)-4-piperidyl]ethyl]spiro[[1,3]dioxolo[4,5-f]isoindole-7,1'-cyclopropane]-5-one (I-38);

6-[2-[1-(1H-pyrrol-2-ylmethyl)-4-piperidyl]ethyl]spiro[[1,3]dioxolo[4,5-f]isoindole-7,1'-cyclopropane]-5-one (I-39);

6-[2-[1-[(5-methyl-1H-pyrrol-2-yl)methyl]-4-piperidyl]ethyl]spiro[[1,3]dioxolo[4,5-f]isoindole-7,1'-cyclopropane]-5-one (I-40);

6-[2-[1-(1H-pyrazol-5-ylmethyl)-4-piperidyl]ethyl]spiro[[1,3]dioxolo[4,5-f]isoindole-7,1'-cyclopropane]-5-one (I-41);

or a pharmaceutically acceptable salt thereof.

15. The compound according to claim 1, wherein said compound is:

6-[2-[1-(2-pyridylmethyl)-4-piperidyl]ethyl]spiro[[1,3]dioxolo[4,5-f]isoindole-7,1'-cyclopropane]-5-one (I-29)

or a pharmaceutically acceptable salt thereof.

16. The compound according to claim 15, wherein said compound is:

6-[2-[1-(2-pyridylmethyl)-4-piperidyl]ethyl]spiro[[1,3]dioxolo[4,5-f]isoindole-7,1'-cyclopropane]-5-one (I-29);

6-[2-[1-(2-pyridylmethyl)-4-piperidyl]ethyl]spiro[[1,3]dioxolo[4,5-f]isoindole-7,1'-cyclopropane]-5-one hydrochloride (I-33); or 6-[2-[1-(2-pyridylmethyl)-4-piperidyl]ethyl]spiro[[1,3]dioxolo[4,5-f]isoindole-7,1'-cyclopropane]-5-one phosphate (I-35).

17. A pharmaceutical composition comprising an effective amount of the compound represented by formula (I) or a pharmaceutically acceptable salt thereof according to claim 1.

18. The method of treating Alzheimer's disease comprising administering to a subject in need thereof a therapeutically effective amount of a compound of claim 1.

19. A method for preparing the compound of formula (I) according to claim 1, comprising reacting a compound represented by formula II or a salt thereof with a compound represented by formula III-1 or III-2:

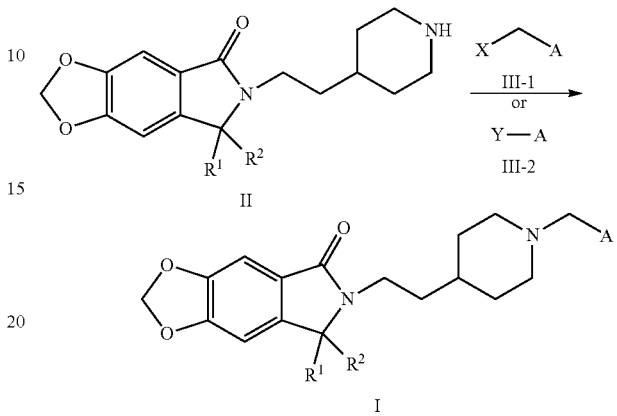

Wherein, $R^1$, $R^2$ and A are as defined in claim 1; X is halogen or hydroxyl; and Y is formyl or alkoxycarbonyl.

20. The method according to claim 19, wherein the compound of formula (II) or a salt thereof is prepared according to the following method, comprising removal of the amino-protecting group in the compound represented by formula IV:

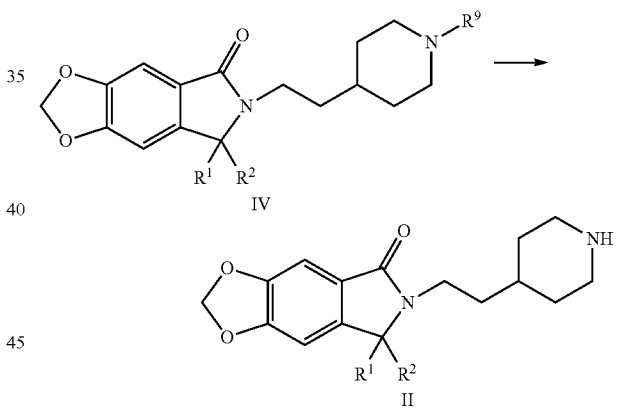

wherein, $R^1$ and $R^2$ are as defined in claim 1; $R^9$ is selected from an amino-protecting group or tert-butoxycarbonyl (Boc).

21. The method according to claim 20, wherein the compound of formula IV wherein $R^1$ and $R^2$ together are =O, i.e., the compound of formula IV-1, is prepared according to the following method, comprising reacting the compound represented by formula V and the compound represented by formula VI:

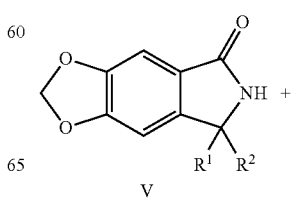

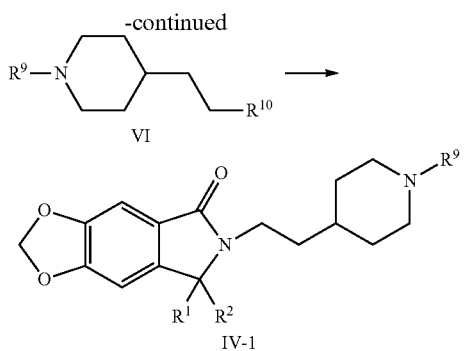

Wherein, $R^1$ and $R^2$ together are =O; $R^9$ is selected from an amino-protecting group or tert-butoxycarbonyl (Boc); and $R^{10}$ is selected from halogen or tosyloxy.

22. The method according to claim 20, wherein the compound of formula IV wherein $R^1$ and $R^2$ are each hydrogen, i.e., the compound of formula IV-2, is prepared according to the following method, comprising first reducing the compound represented by formula IV-1 to an alcohol, and then converting the resultant hydroxyl to an easily leavable acetoxy group, and finally removing the acetoxy group by catalytic hydrogenolysis:

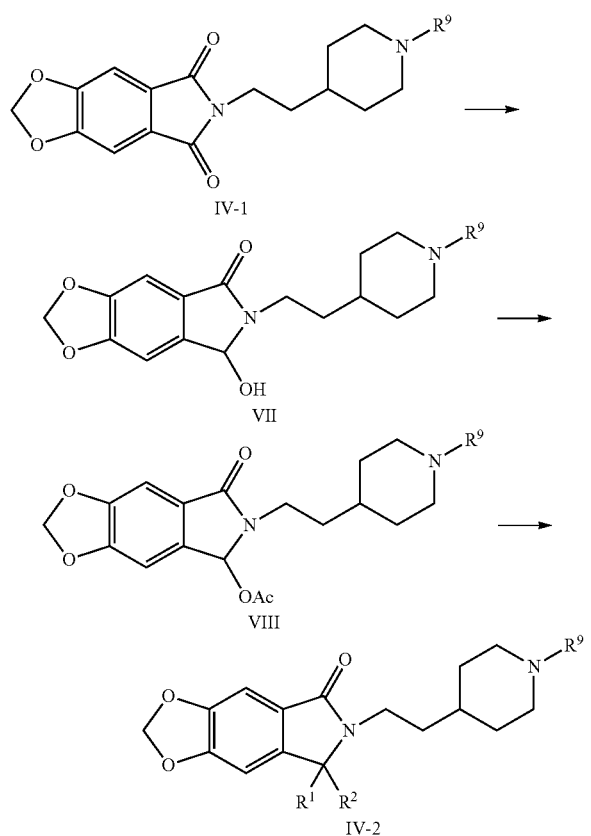

wherein, $R^1$ and $R^2$ are each hydrogen; $R^9$ is selected from an amino-protecting group or tert-butoxycarbonyl (Boc).

23. The method according to claim 20, wherein the compound of formula IV wherein $R^1$ is methyl or ethyl, and $R^2$ is hydrogen, i.e., the compound of formula IV-3, is prepared according to the following method, comprising carrying out mono-alkylation of the methylene group in the 5-membered lactam in the compound represented by formula IV-2:

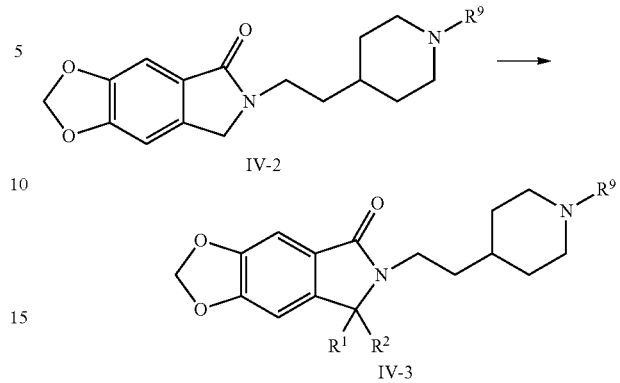

Wherein, $R^1$ is methyl or ethyl, and $R^2$ is hydrogen; $R^9$ is selected from an amino-protecting group or tert-butoxycarbonyl (Boc).

24. The method according to claim 20, wherein the compound of formula IV wherein $R^1$ and $R^2$ are each independently methyl or ethyl, i.e., the compound of formula IV-4, is prepared according to the following method, comprising carrying out further alkylation of the carbon atom connecting $R^1$ in the compound represented by formula IV-3:

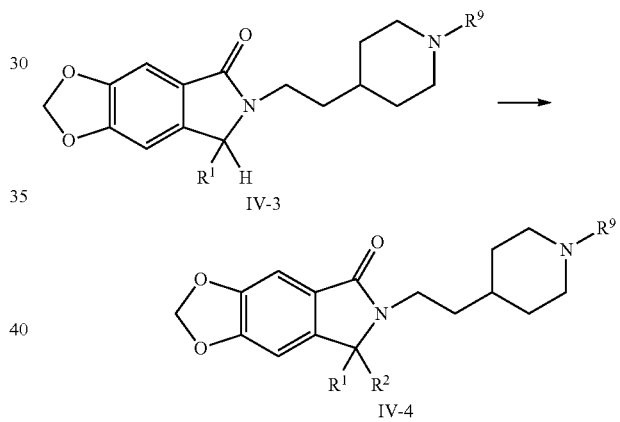

Wherein, $R^1$ and $R^2$ are each independently methyl or ethyl; $R^9$ is selected from an amino-protecting group or tert-butoxycarbonyl (Boc).

25. The method according to claim 20, wherein the compound of formula IV wherein $R^1$ and $R^2$ together with the carbon atom connecting them form a 3-membered carbon ring, i.e., the compound of formula IV-5, is prepared according to the following method, comprising first reacting the compound represented by formula IV-1 with methyl Grignard reagent to form an alcohol, and then dehydrating the resultant alcohol to an alkene under acidic conditions, finally converting the generated carbon-carbon double bond to a 3-membered ring by using $Et_2Zn/TFA/CH_2I_2$:

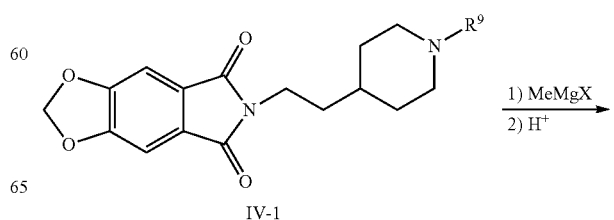

-continued
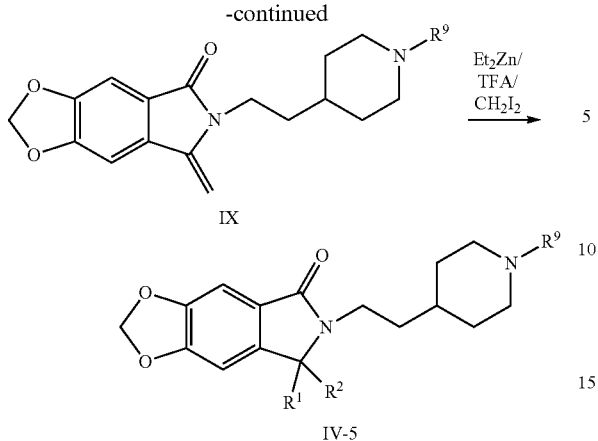
Wherein, $R^1$ and $R^2$ together with the carbon atom connecting them form a 3-membered carbon ring; $R^9$ is selected from an amino-protecting group or tert-butoxycarbonyl (Boc); X is halogen.
* * * * *